United States Patent
Boyman et al.

(10) Patent No.: US 10,894,828 B2
(45) Date of Patent: Jan. 19, 2021

(54) IMMUNE-STIMULATING MONOCLONAL ANTIBODIES AGAINST HUMAN INTERLEUKIN-2

(71) Applicants: Onur Boyman, Küsnacht (CH); Natalia Arenas-Ramirez, Zürich (CH); Chao Zou, Basel (CH)

(72) Inventors: Onur Boyman, Küsnacht (CH); Natalia Arenas-Ramirez, Zürich (CH); Chao Zou, Basel (CH)

(73) Assignee: Universität Zürich, Zürich (CH)

( * ) Notice: Subject to any disclaimer, the term of this patent is extended or adjusted under 35 U.S.C. 154(b) by 250 days.

(21) Appl. No.: 15/324,468

(22) PCT Filed: Jul. 10, 2015

(86) PCT No.: PCT/IB2015/055226
§ 371 (c)(1),
(2) Date: Jan. 6, 2017

(87) PCT Pub. No.: WO2016/005950
PCT Pub. Date: Jan. 14, 2016

(65) Prior Publication Data
US 2017/0183403 A1 Jun. 29, 2017

(30) Foreign Application Priority Data
Jul. 10, 2014 (EP) .................................. 14176619

(51) Int. Cl.
| | | |
|---|---|---|
| *A61K 38/20* | (2006.01) | |
| *A61K 39/395* | (2006.01) | |
| *A61K 39/00* | (2006.01) | |
| *C07K 14/55* | (2006.01) | |
| *C07K 16/24* | (2006.01) | |

(52) U.S. Cl.
CPC ........ *C07K 16/246* (2013.01); *A61K 38/2013* (2013.01); *A61K 39/3955* (2013.01); *C07K 14/55* (2013.01); *A61K 2039/505* (2013.01); *C07K 2317/34* (2013.01); *C07K 2317/55* (2013.01); *C07K 2317/565* (2013.01); *C07K 2317/74* (2013.01); *C07K 2317/76* (2013.01); *C07K 2317/92* (2013.01)

(58) Field of Classification Search
CPC ............ A61K 38/2013; A61K 39/3955; A61K 2039/505; C07K 14/55; C07K 2317/34; C07K 2317/55; C07K 2317/74; C07K 2317/76; C07K 2317/92
See application file for complete search history.

(56) References Cited

U.S. PATENT DOCUMENTS

| | | | |
|---|---|---|---|
| 6,111,090 | A | 8/2000 | Gorman et al. |
| 7,025,962 | B1 | 4/2006 | Gorman et al. |
| 2008/0286269 | A1 | 11/2008 | Violette et al. |
| 2013/0142806 | A1 | 6/2013 | Lu et al. |

FOREIGN PATENT DOCUMENTS

| | | |
|---|---|---|
| CA | 1340853 C | 12/1999 |
| EP | 1947183 B1 | 7/2013 |
| WO | 2004060319 A2 | 7/2004 |
| WO | 2006083289 A2 | 8/2006 |
| WO | 2006128690 A1 | 12/2006 |
| WO | 2009101611 A1 | 8/2009 |
| WO | 2012107417 A1 | 8/2012 |
| WO | 2013157105 A1 | 10/2013 |
| WO | 2014012479 A1 | 1/2014 |

OTHER PUBLICATIONS

Letourneau, S., et al. IL-2/IL-2 antibody complexes show strong biological activity by avoiding interaction with IL-2 receptor alpha subunit CD25. Proc. Natl. Acad. Sci. USA, 2010, vol. 105, No. 5, p. 2171-2176.*
Bendig, M.M. Humanization of roden monoclonal antibodies by CDR grafting. Methods: A Companion to Methods in Enzymology, 1995, 8:83-93.*
Casset, F., et al. A peptide mimetic of an anti-CD4 monoclonal antibody by rational design. Biochem. Biophys. Res. Comm., 2003, 307:198-205.*
MacCallum, R.M., et al. Antibody-antigen interactions: Contact analysis and binding site topography. J. Mol. Biol., 1998, 262:732-745.*
Paul. W.E. Fundamental Immunology, 3rd Ed., 1993, p. 292-295.*
Rudikoff, S., et al. Single amino acid substitution altering antigen-binding specificity. Proc. Natl. Acad. Sci. USA, 1982, 79:1979-1983.*
Vajdos, F.F., et al. Comprehensive functional maps of the antigen-binding site of an anti-ErbB2 antibody obtained with shotgun scanning mutagenesis. J. Mol. Biol., 2002, 320:415-428.*
Wu, H., et al. Humanization of a murine monoclonal antibody by simultaneous optimization of framework and CDR residues J. Mol. Biol., 1999, 294:151-162.*
European Office Action dated Nov. 14, 2017 and received in European Application No. 15759938.2.

(Continued)

*Primary Examiner* — Vanessa L. Ford
*Assistant Examiner* — Bruce D. Hissong
(74) *Attorney, Agent, or Firm* — Michele M. Wales; Inhouse Patent Counsel, LLC

(57) ABSTRACT

The invention relates to a human Interleukin-2 (hIL-2) specific monoclonal antibody (mAb), or antigen binding fragment thereof, the binding of which to hIL-2 inhibits binding of hIL-2 to CD25 and the antibody is characterized by any of the parameters: the variable chain of the mAb comprises the amino acid sequence of SEQ ID NO 005 or SEQ ID NO 006; the binding to hIL-2 is characterized by a dissociation constant $(K_D) \leq 7.5$ nmol/L; the binding to hIL-2 is characterized by an off-rate $(K_{off}) \leq 1 \times 10^{-4}$ s$^{-1}$ and/or the antibody displays no measurable cross-reactivity to murine IL-2.

25 Claims, 14 Drawing Sheets

Specification includes a Sequence Listing.

(56) References Cited

OTHER PUBLICATIONS

Schwartzentruber, et al., "In Vitro Predictors of Therapeutic Response in Melanoma Patients Receiving Tumor-Infiltrating Lymphocytes and Interleukin-2", Jul. 1, 1994.
Tomala, et al., "Chimera of IL-2 Linked to Light Chain of Anti-IL-2 mAb Mimics IL-2/anti-IL-2 mAb Complexes Both Structurally and Functionally"; Feb. 18, 2013.
Tomala, et al., "In Vivo Expansion of Activated Naïve CD8+T Cells and NK Cells Driven by Complexes f IL-2 and Anti-IL-2 Monoclonal Antibody As Novel Approach of Cancer Immunotherapy", 2009.
Corrected Version of Krieg, et al.,"Improved IL-2 Immunotherapy by Selective Stimulation of IL-2 Receptors on Lymphocytes and Endothelial Cells", PNAS, vol. 107, No. 26, May 19, 2010, pp. 11906-11911 (XP002738483).
Budd et al., "Interleukin-2 Monoclonal Antibody Affinity Adsorption", Journal of Immunological Methods, vol. 95, pp. 237-248, (1986).
EP application corresponding to SYO62-26969 8 in corresponding JP Application 62-269698.
Ide et al., "Neutralizing Monoclonal Antibodies Against Recombinant Human Interleukin-2", Journal of Immunological Methods, vol. 101, pp. 57-62, (1987).
Al-Lazikani et al., "Standard Conformations for the Canonical Structures of Immunoglobulins", J. Mol. Biol, vol. 273, pp. 927-948 (1997).
Arenas-Ramirez et al., "Improved Cancer Immunotherapy by a CD25-Mimobody Conferring Selectivity to Human Interleukin-2", Sci. Trans!. Med., vol. 8, pp. 1-12 (2016).
Jones et al., "Replacing the Complementarity-Determining Regions in a Human Antibody with those from a Mouse", Nature, vol. 321, pp. 522-525 (1986).
Levin et aL, "Exploiting a Natural Conformational Switch to Engineer an Interleukin-2 Superkine", Nature, vol. 484 pp. 529-533 (2012).
Queen et aL, "A Humanized Antibody that Binds to the Interleukin 2 Receptor", Proc. Natl. Acad. Sci, vol. 86, pp. 10029-10033 (1989).
Nang et al., "Structure of the Quaternary Complex of Interleukin-2 with Its $\alpha$, $\beta$, and Yc Receptors", Science, vol. 310, pp. 1159-1163 (2005).

* cited by examiner

IMMUNE-STIMULATING MONOCLONAL ANTIBODIES AGAINST HUMAN INTERLEUKIN-2

CROSS-REFERENCE TO RELATED APPLICATIONS

This is application is a 35 USC § 371 National Stage Application of International Application No. PCT/IB2015/055226, filed Jul. 10, 2015, which claims benefit of European Application No. 14176619.6, filed Jul. 10, 2014, each of which are herein incorporated by reference in their entireties.

SEQUENCE LISTING

The instant application contains a Sequence Listing which has been filed electronically in ASCII format and is hereby incorporated by reference in its entirety. Said ASCII copy, created on Jan. 4, 2017, is named PAT056093_ST25.txt and is 39,591 bytes in size.

The instant application contains a Sequence Listing which has been filed electronically in ASCII format and is hereby incorporated by reference in its entirety. Said ASCII copy, created on Jan. 4, 2017, is named PAT056093_ST25.txt and is 39,591 bytes in size.

FIELD OF THE INVENTION

The present invention relates to antibodies binding to human interleukin-2 (hIL-2). The invention more specifically relates to antibodies specifically binding a particular epitope of hIL-2 and when bound to this epitope are capable of inhibit binding of hIL-2 to CD25. Furthermore, the invention relates to in vitro and in vivo therapeutic applications of the antibodies.

BACKGROUND OF THE INVENTION

Malignant melanoma is a frequent cancer type in men and women. Once melanoma becomes metastatic and spreads to distant sites, the 5-year survival rate is quite poor, calculated at about 15%. Currently available treatment strategies for metastatic melanoma barely improve this survival rate.

Interleukin-2 (IL-2) is a cytokine able to potently stimulate cytotoxic lymphocytes against metastatic tumours. However, IL-2 is also able to stimulate so-called $CD25^+$ $CD4^+$ regulatory T cells (Treg cells) that are crucial for prevention of autoimmune disease. Importantly, Treg cells can significantly dampen anti-tumour responses by cytotoxic lymphocytes, thus somewhat antagonizing the beneficial anti-tumour effects of IL-2. Moreover, at doses required to achieve a clinical anti-tumour response, IL-2 can exert toxic adverse effects.

Standard IL-2 immunotherapy has been used since the early 1980's for the immunotherapy of metastatic melanoma and metastatic renal cell carcinoma, leading to the approval by the FDA for these indications in 1996 and 1992, respectively. While IL-2 given at high doses has shown objective response rates in about 17% and complete regression in about 6-9% of patients suffering from these deadly metastatic cancers, IL-2 given at these doses frequently led to toxic adverse effects, such as hypotension, pulmonary edema, liver cell damage, gastrointestinal toxicity, and general edema. Moreover, as mentioned above, IL-2 is able to stimulate Treg cells, which in turn are able to dampen the activity of anti-tumour $CD8^+$ T cells and NK cells.

The combination of IL-2 with a particular anti-IL-2 monoclonal antibody (mAb) has been shown to improve IL-2 therapy in experimental murine models of cancer immunotherapy by
(1) directing IL-2 preferentially to cytotoxic lymphocytes, but not Treg cells, and by
(2) rendering IL-2 more potent but less toxic (Boyman O, Kovar M, Rubinstein M P, Surh C D, and Sprent J. Selective stimulation of T cell subsets with antibody-cytokine immune complexes. *Science* (2006) 311:1924-1927; Krieg C, Letourneau S, Pantaleo G, and Boyman O. Improved IL-2 immunotherapy by selective stimulation of IL-2 receptors on lymphocytes and endothelial cells. *Proceedings of the National Academy of Sciences USA* (2010) 107:11906-11911).

This approach has the advantage that unmutated, natural IL-2 is delivered via anti-IL-2 mAb to $CD8^+$ T cells and NK cells, which subsequently exert potent anti-tumour properties, while IL-2 complexed to this kind of anti-IL-2 mAb barely activates Treg cells. Moreover, IL-2 complexed to this kind of anti-IL-2 mAb is much less toxic than standard IL-2 immuno therapy in mice. However, this therapy has up to date not been available for use in patients due to the lack of appropriate anti-human IL-2 mAbs.

SUMMARY OF THE INVENTION

The problem addressed by the present invention is to provide an anti-human IL-2 monoclonal antibody able to recognize and bind a specific epitope of human IL-2, thereby favoring the stimulation of cytotoxic T cells and NK cells compared to Treg cells, for use in in vitro and in vivo therapeutic applications. This problem is solved by the subject-matter of the independent claims.

According to a first aspect of the invention a human interleukin-2 (hIL-2) specific monoclonal antibody (mAb), or antigen binding fragment thereof, is provided, wherein the antibody is able to bind to a particular epitope in hIL-2 thereby inhibiting the binding to CD25, thus modulating the immunological effects of hIL-2/IL-2R interaction. The antibody of the invention is further characterized by at least one of the parameters:

a) the variable chain of the mAb comprises an amino acid sequence having an identity of ≥85%, ≥90%, ≥95%, or ≥99% compared to SEQ ID NO 005 or SEQ ID NO 006;

b) the antibody binding to hIL-2 is, i.e. the reaction mAb+hIL-2⇔mAb*hIL-2, wherein mAb*hIL-2 symbolizes the bound complex of antibody and interleukin, is characterized by a dissociation constant $(K_D)$≤7.5 nmol/L, ≤5 nmol/L, ≤3 nmol/L, ≤2 nmol/L or ≤1.5 nmol/L;

c) the antibody binding to hIL-2 is characterized by an off-rate $(K_{off})$≤1×10$^{-4}$ s$^{-1}$, ≤8×10$^{-5}$ s$^{-1}$, ≤6×10$^{-5}$ s$^{-1}$, ≤4×10$^{-5}$ s$^{-1}$, ≤3×10$^{-5}$ s$^{-1}$ or ≤2.1×10$^{-5}$ s$^{-1}$;

d) upon mAb binding to hIL-2, the resulting mAb*hIL-2 complex cannot efficiently bind human IL-2 receptor α (also known as CD25) anymore, effectively rendering the binding of human CD25 to mAb*hIL-2 to background levels as compared to the binding of human CD25 to free (non-complexed) hIL-2 when measured by surface plasmon resonance; and/or e) the antibody displays no measurable cross-reactivity to murine IL-2.

A lack of cross-reactivity with murine IL-2 is advantageous for preclinical studies, which usually involve mouse models, such as the use of mAb*hIL-2 complexes for the treatment of murine tumour models where a cross-reactive anti-IL-2 mAb might bind and seclude endogenous murine IL-2 from endogenous murine Treg cells, thus enhancing the anti-tumour response.

A lack of cross-reactivity with murine IL-2 is also advantageous for preclinical safety and efficacy studies conducted prior to development of a candidate mAb in human patients.

In certain embodiments the hIL-2 mAb comprises at least one $V_H$ and/or $V_L$ sequence having an identity of ≥80%, ≥85%, ≥90%, ≥92%, ≥93%, ≥94%, ≥95%, ≥96%, ≥97% or ≥98% compared to SEQ ID NOs 019 or SEQ ID NO 020.

In certain embodiments the variable chain of the hIL-2 mAb comprises an amino acid sequence having an identity of ≥85%, ≥90%, ≥95%, or ≥99% compared to SEQ ID NOs 003, 004, 005 or 006 and the hIL-2 mAb is characterized by a dissociation constant ≤7.5 nmol/L, ≤5 nmol/L, ≤3 nmol/L, ≤2 nmol/L or ≤1.5 nmol/L.

In certain embodiments the variable chain of the hIL-2 mAb comprises an amino acid sequence having an identity of ≥85%, ≥90%, ≥92%, ≥93%, ≥94%, ≥95%, ≥96%, ≥97%, ≥98% or ≥99% compared to SEQ ID NO 005 or 006 and the hIL-2 mAb is characterized by an off-rate ≤1×10$^{-4}$ s$^{-1}$, ≤8×10$^{-5}$ s$^{-1}$, ≤6×10$^{-5}$ s$^{-1}$, ≤4×10$^{-5}$ s$^{-1}$, ≤3×10$^{-5}$ s$^{-1}$ or ≤2.1×10$^{-5}$ s$^{-1}$.

In certain embodiments the variable chain of the hIL-2 mAb comprises an amino acid sequence having an identity of ≥85%, ≥90%, ≥92%, ≥93%, ≥94%, ≥95%, ≥96%, ≥97%, ≥98% or ≥99% compared to SEQ ID NO 005 or 006 and the hIL-2 mAb displays no measurable cross-reactivity to murine IL-2.

In certain embodiments the sequence of the hIL-2 mAb is humanized for administration to human patients to prevent adverse reactions.

In certain embodiments the hIL-2 mAb is provided as fragment antigen-binding (Fab) or single-chain variable fragment (scFv).

In certain embodiments the hIL-2 mAb comprises at least one complementarity determining (CDR) sequence having an identity of ≥80%, ≥85%, ≥90%, ≥92%, ≥93%, ≥94%, ≥95%, ≥96%, ≥97% or ≥98% compared to SEQ ID NOs 007, 008, 009, 010, 011 or 012.

According to a second aspect of the invention, a nucleic acid molecule encoding the monoclonal antibody, or antigen binding fragment thereof, able to bind to human interleukin-2 according to the first aspect of the invention is provided.

In certain embodiments the nucleic acid molecule according to the second aspect of the invention has ≥60%, ≥70%, ≥80%, ≥90%, ≥95%, or ≥99% sequence identity compared to SEQ ID NOs 003 to 004.

According to a third aspect of the invention a vector comprising the nucleic acid molecule according to the invention is provided.

According to a fourth aspect of the invention, a cell is provided, comprising or expressing the nucleic acid molecule according to the invention.

According to a fifth aspect of the invention a cell able to produce the antibodies according to the first aspect of the invention is provided.

According to a sixth aspect of the invention a monoclonal antibody-producing hybridoma cell line is provided, characterized in that the antibodies produced are those of the first aspect of the invention.

According to a seventh aspect of the invention a therapeutic formulation for use in the treatment of cancer or other diseases benefiting from immune stimulatory therapy, such as viral infections, comprising i. the monoclonal antibody (mAb) according to the first aspect of the invention, and/or
ii. human interleukin-2 or human IL-2 mutants, administered to the subject either contemporaneously or at different time points.

According to an eighth aspect of the invention a fusion protein is provided. The fusion protein comprises:
a. an hIL-2 binding polypeptide fragment, wherein said polypeptide is characterized by any one of the parameters:
    i. the hIL-2 binding polypeptide fragment comprises an amino acid sequence having an identity of ≥85%, ≥90%, ≥92%, ≥93%, ≥94%, ≥95%, ≥96%, ≥97% or ≥98% compared to SEQ ID NO 021 or SEQ ID NO 022;
    ii. the hIL-2 binding of said polypeptide fragment to hIL-2 is characterized by a dissociation constant ($K_D$)≤7.5 nmol/L, ≤5 nmol/L, ≤3 nmol/L, ≤2 nmol/L or ≤1.5 nmol/L;
    iii. the binding of said hIL-2 binding polypeptide fragment to hIL-2 is characterized by an off-rate ($K_{off}$)≤1×10$^{-4}$ s$^{-1}$, ≤8×10$^{-5}$ s$^{-1}$, ≤6×10$^{-5}$ s$^{-1}$, ≤4×10$^{-5}$ s$^{-1}$, ≤3×10$^{-5}$ s$^{-1}$ or 2.1×10$^{-5}$ s$^{-1}$;
    and/or
    iv. the hIL-2 binding polypeptide fragment displays no measurable crossreactivity to murine IL-2.
b. a human IL-2 polypeptide fragment having an identity of ≥85%, ≥90%, ≥92%, ≥93%, ≥94%, ≥95%, ≥96%, ≥97% or ≥98% compared to SEQ ID NO 001, and, optionally,
c. an amino acid linker of 1 to 50, particularly of 5 to 40, more particularly of 10 to 30, even more particularly of approx. 15 to 25 amino acids, linking the hIL-2 binding polypeptide fragment to the human IL-2 polypeptide fragment as one single polypeptide chain.

In other words the fusion protein retains the ability of the antibody to bind and direct human interleukin-2 to stimulate selected immune cells, such as CD8$^+$ T cells and NK cells.

The advantage of using such fusion protein is that human IL-2 will not be able to dissociate from the antibody and that the therapy will be composed of one single product instead of two, facilitating various aspects of manufacture, dosing and regulatory compliance.

According to a ninth aspect of the invention, an isolated antibody or antigen binding fragment thereof binding a specific epitope is provided. Said epitope can be the epitope to which an isolated antibody or antigen binding fragment thereof according to other aspects of the invention binds. In an embodiment, the isolated antibody or molecule binds to a human interleukin-2 (hIL-2) epitope which comprises the amino acids K52, P54, K55, T57, R58, T61, F62, K63, Q94, and K96. In another embodiment, the isolated antibody or molecule binds to an epitope further comprising any one or more of the amino acids N50, N53, N91, L92, A93, and N97. An isolated antibody or molecule, which comprises an antigen recognition surface having epitope recognition characteristics equivalent to an antibody or antigen binding fragment thereof according to other aspects is also provided.

Wherever alternatives for single separable features such as, for example, a coding sequence or binding epitope are laid out herein as "embodiments", it is to be understood that such alternatives may be combined freely to form discrete embodiments of the invention disclosed herein.

The invention is further illustrated by the following examples and figures, from which further embodiments and advantages can be drawn. These examples are meant to illustrate the invention but not to limit its scope.

Definitions

By "human interleukin-2" or "hIL-2" is meant the protein designated UniProt ID P60568 and is reproduced as SEQ ID NO: 1.

Identity in the context of the present specification is a single quantitative parameter representing the result of a sequence comparison position by position. Methods of sequence comparison are known in the art; the BLAST algorithm available publicly is an example. One such example for comparison of nucleic acid sequences is the BLASTN algorithm that uses the default settings: Expect threshold: 10; Word size: 28; Max matches in a query range: 0; Match/Mismatch Scores: 1.-2; Gap costs: Linear. In the absence of other measurement variables, identity shall be measured according to the specification above.

In the context of the present specification, the term antibody is used in its meaning known in the art of cell biology and immunology; it refers to whole antibodies, any antigen binding fragment or single chains thereof and related or derived constructs. A whole antibody is a glycoprotein comprising at least two heavy (H) chains and two light (L) chains interconnected by disulfide bonds. Each heavy chain is comprised of a heavy chain variable region ($V_H$) and a heavy chain constant region ($C_H$). The heavy chain constant region is comprised of three domains, $C_H1$, $C_H2$ and $C_H3$. Each light chain is comprised of a light chain variable region (abbreviated herein as $V_L$) and a light chain constant region ($C_L$). The light chain constant region is comprised of one domain, $C_L$. The $V_H$ and $V_L$ regions can be further subdivided into regions of hypervariability, termed complementarity determining regions 20 (CDR), interspersed with regions that are more conserved, termed framework regions (FR). Each $V_H$ and $V_L$ is composed of three CDRs and four FRs arranged from amino-terminus to carboxyterminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component of the classical complement system.

In the context of the present specification, the term antigen binding portion or antigen binding fragment is used in its meaning known in the art of cell biology and immunology; it refers to one or more fragments of an intact antibody that retain the ability to specifically bind to a given antigen (e.g., interleukin-2). Antigen binding functions of an antibody can be performed by fragments of an intact antibody. Examples of binding fragments encompassed within the term antigen binding portion or antigen binding fragment of an antibody include a Fab fragment, a monovalent fragment consisting of the $V_L$, $V_H$, $C_L$ and $C_H$ domains; a $F(ab)_2$ fragment, a bivalent fragment comprising two Fab fragments linked by a disulfide bridge at the hinge region; an Fd fragment consisting of the $V_H$ and $C_H$ domains; an Fv fragment consisting of the $V_L$ and $V_H$ domains of a single arm of an antibody; a single domain antibody (dAb) fragment, which consists of a $V_H$ domain or a $V_L$ domain; and an isolated complementarity determining region (CDR). HCDR means a CDR of the heavy chain and LCDR means a CDR of the light chain.

In the context of the present specification, the term chimeric antibody is used in its meaning known in the art of cell biology and immunology; it refers to an antibody molecule in which the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, cytokine, toxin, hormone, growth factor, drug, etc. For example, an antibody can be modified by replacing its constant region with a cytokine. Due to the replacement with a cytokine, the chimeric antibody can retain its specificity in recognizing the antigen while having also the function, or part thereof, of the original cytokine molecule.

In the context of the present specification, the term hybridoma is used in its meaning known in the art of cell biology and biochemistry; it refers to a hybrid cell created by fusion of a specific antibody-producing B-cell with a myeloma (B-cell cancer) cell. Hybridoma cells can be grown in tissue culture and produce antibodies of a single specificity (monoclonal antibodies).

In the context of the present specification, the term single-chain variable fragment (scFv) is used in its meaning known in the art of cell biology and biochemistry; it refers to a fusion protein of the variable regions of the heavy ($V_H$) and light chains ($V_L$) of immunoglobulins, connected with a short linker peptide of ten to about 25 amino acids. The scFv retains the specificity of the original immunoglobulin, despite removal of the constant regions and the introduction of the linker.

In the context of the present specification, the term fragment antigen-binding (Fab) is used in its meaning known in the art of cell biology and immunology; it refers to a region on an antibody that binds to antigens. It is composed of one constant and one variable domain of each of the heavy ($V_H$) and light chains ($V_L$) of immunoglobulins. These domains shape the antigen-binding site at the amino terminal end of the monomer.

In the context of the present specification, the term dissociation constant ($K_D$) is used in its meaning known in the art of chemistry and physics; it refers to an equilibrium constant that measures the propensity of a larger object to dissociate reversibly into smaller components, as when a complex falls apart into its component molecules. $K_D$ is expressed in molar units [M] and corresponds to the concentration of [Ab] at which the binding sites of [Ag] are half occupied. In other words the concentration of unbound [Ab] equals the concentration of the [AbAg] complex. The dissociation constant can be calculated according to the following formula:

$$K_D = \frac{[Ab] * [Ag]}{[AbAg]}$$

[Ab]: concentration of antibody; [Ag]: concentration of antigen; [AbAg]: concentration of antibodyantigen complex In the context of the present specification, the terms off-rate (Koff; [1/sec]) and on-rate (Kon; [1/sec*M]) are used in their meaning known in the art of chemistry and physics; they refer to a rate constant that measures the dissociation (Koff) or association (Kon) of 5 an antibody with its target antigen. Koff and Kon can be experimentally determined using methods well established in the art. A method for determining the Koff and Kon of an antibody employs surface plasmon resonance. This is the principle behind biosensor systems such as the Biacore® or the ProteOn® system. They can also be used to determine the dissociation constant KD by using the following formula:

$$K_D = \frac{[K_{off}]}{[K_{on}]}$$

In the context of the present specification, the term humanized antibodies is used in its meaning known in the art of cell biology and biochemistry; it refers to antibodies originally produced by immune cells of a non-human species, whose protein sequences have been modified to increase their similarity to antibody variants produced naturally in humans.

In the context of the present specification, the term no measurable cross-reactivity refers to the lacking capability of an antibody to recognize and bind to orthologous proteins from other species. For example, an antibody directed against human interleukin-2 would have no measurable cross-reactivity to murine interleukin-2 if, under suitable conditions, binding of the antibody to murine interleukin-2 could not be detected with sufficiently sensitive methods such as surface plasmon resonance. One such example of no measurable cross-reactivity is shown in FIG. 9 for the antibody in the lower panel (NARA1).

As used herein, an antibody or a protein that "specifically binds to hIL-2" is intended to refer to an antibody or protein that binds to human IL-2 polypeptide with a $K_D$ of 100 nM or less, 10 nM or less, 1 nM or less, 100 pM or less, or 10 pM or less. An antibody that "cross-reacts with an antigen other than human IL-2" is intended to refer to an antibody that binds that antigen with a $K_D$ of 10 nM or less, 1 nM or less, or 100 pM or less. An antibody that "does not cross-react with a particular antigen" is intended to refer to an antibody that binds to that antigen, with a $K_D$ of 100 nM or greater, or a $K_D$ of 1 µM or grater, or a $K_D$ of 10 µM or greater. In certain embodiments, such antibodies that do not cross-react with the antigen exhibit essentially undetectable binding against these proteins in standard binding assays.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

The term "epitope binding domain" or "EBD" refers to portions of a binding molecule (e.g., an antibody or epitope-binding fragment or derivative thereof), that specifically interacts with (e.g., by binding, steric hindrance, stabilizing/destabilizing, spatial distribution) a binding site on a target epitope. EBD also refers to one or more fragments of an antibody that retain the ability to specifically interact with (e.g., by binding, steric hindrance, stabilizing/destabilizing, spatial distribution) a IL-2 epitope and inhibit signal transduction. Examples of antibody fragments include, but are not limited to, an scFv, a Fab fragment, a monovalent fragment consisting of the VL, VH, CL and CH1 domains; a F(ab)$_2$ fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; a dAb fragment (Ward et al., (1989) Nature 341:544-546), which consists of a VH domain; and an isolated complementarity determining region (CDR).

EBDs also include single domain antibodies, maxibodies, unibodies, minibodies, triabodies, tetrabodies, v-NAR and bis-scFv, as is known in the art (see, e.g., Hollinger and Hudson, (2005) Nature Biotechnology 23: 1126-1136), bispecific single chain diabodies, or single chain diabodies designed to bind two distinct epitopes. EBDs also include antibody-like molecules or antibody mimetics, which include, but not limited to minibodies, maxybodies, Fn3 based protein scaffolds, Ankrin repeats (also known as DARpins), VASP polypeptides, Avian pancreatic polypeptide (aPP), Tetranectin, Affililin, Knottins, SH3 domains, PDZ domains, Tendamistat, Neocarzinostatin, Protein A domains, Lipocalins, Transferrin, and Kunitz domains that specifically bind epitopes, which are within the scope of the invention. Antibody fragments can be grafted into scaffolds based on polypeptides such as Fibronectin type III (Fn3) (see U.S. Pat. No. 6,703,199, which describes fibronectin polypeptide monobodies).

The present invention also encompasses an antibody to human IL-2, which is an isolated antibody.

The phrase "isolated antibody", as used herein, refers to antibody that is substantially free of other antibodies having different antigenic specificities (e.g., an isolated antibody that specifically binds hIL-2 is substantially free of antibodies that specifically bind antigens other than hIL-2). An isolated antibody that specifically binds hIL-2 may, however, have cross-reactivity to other antigens, such as IL-2 molecules from other species. Moreover, an isolated antibody may be substantially free of other cellular material and/or chemicals.

The terms "nucleic acid" and "polynucleotide" or "nucleotide coding sequences" are used interchangeably and refer to a polymeric form of nucleotides of any length, either deoxyribonucleotides or ribonucleotides or analogs thereof. Polynucleotides can have any three-dimensional structure and can perform any function. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, siRNAs, shRNAs, RNAi agents, and primers. A polynucleotide can be modified or substituted at one or more base, sugar and/or phosphate, with any of various modifications or substitutions described herein or known in the art. A polynucleotide can comprise modified nucleotides, such as methylated nucleotides and nucleotide analogs. If present, modifications to the nucleotide structure can be imparted before or after assembly of the polymer. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

The term "polypeptide" is used interchangeably with the term "protein" and in its broadest sense refers to a compound of two or more subunit amino acids, amino acid analogs, or peptidomimetics. The subunits can be linked by peptide bonds. In another embodiment, the subunit may be linked by other bonds, e.g., ester, ether, etc.

As used herein, the term "treating" or "treatment" of any disease or disorder (e.g. cancer) refers in one embodiment, to ameliorating the disease or disorder (e.g. slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. Methods for assessing treatment and/or prevention of disease are generally known in the art, unless specifically described hereinbelow.

DETAILED DESCRIPTION OF THE INVENTION

Until now, no monoclonal antibodies suitable for the disclosed invention have been available. The inventors disclose their anti-human IL-2 mAbs that allow the following crucial steps towards the use and commercialization of this technology in clinical applications:

Further sequencing and fine characterization of the anti-human IL-2 mAbs.

Humanization of the anti-human IL-2 mAbs, which is essential to avoid (or minimize) immunogenicity in patients.

Generation of different formats of anti-human IL-2 mAbs, such as IgG, IgG1, IgG4, Fab, and single-chain Fv (scFv).

Generation of a fusion protein consisting of human IL-2 and an anti-human IL-2 mAb (or a fragment of the anti-human IL-2 mAb): such a construct has the advantage of consisting of one component only, instead of two as in IL-2 bound to an anti-human IL-2 mAb.

The inventors have generated and characterized specific anti-human IL-2 mAbs that are able to bind human IL-2 and, when tested in mice, are able to exert specific and potent stimulation of cytotoxic lymphocytes, including CD8$^+$ T cells and natural killer (NK) cells. Towards these ends several difficulties had to be overcome.

Human IL-2 shows high similarity with mouse and rat IL-2, thus human IL-2 is able to stimulate mouse lymphocytes in vitro and in vivo. Moreover, IL-2 is present at high concentrations in the primary immune organs (such as the bone marrow), which is the reason why IL-2 is somewhat a "forbidden" antigen, meaning it is very difficult to generate B cell responses leading to neutralizing antibodies against IL-2. Nevertheless, the inventors were able to elicit polyclonal anti-human IL-2 antibody responses, following immunization of C57BL/6 mice using purified recombinant human IL-2 plus adjuvant.

Of the generated antibody responses, only some mAbs efficiently bound to IL-2 (socalled "binders") and of those only about 0.35% interacted with the presumed active site of IL-2.

Finally, of these anti-human IL-2 mAbs some showed the desired specific and potent in vivo activity as assessed by specialized in vivo assays in mice that are not replaceable by in vitro experiments.

Figure 1:
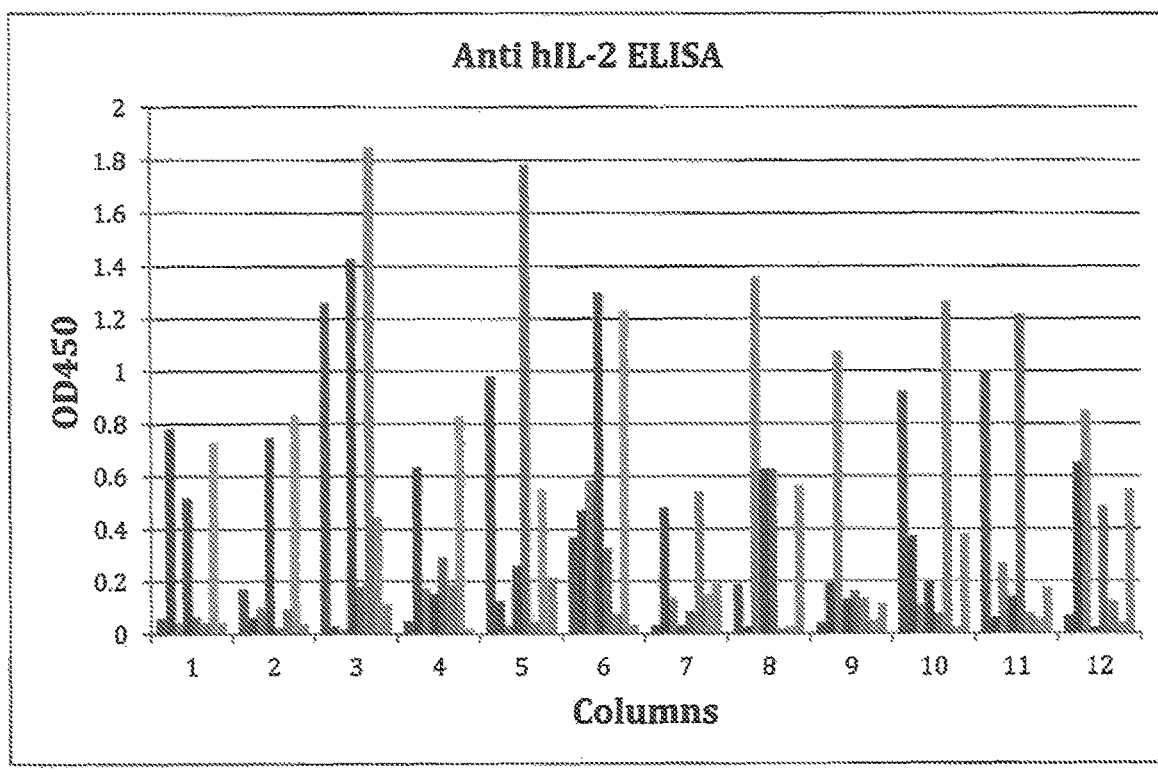
FIG. 1 shows anti-human IL-2 binders. Supernatants of B cell clones obtained after B cell hybridoma fusion were added to a plate previously coated with human IL-2. The anti-human IL-2 mAbs were detected using a biotinylated anti-mouse IgG antibody.
Figure 2:
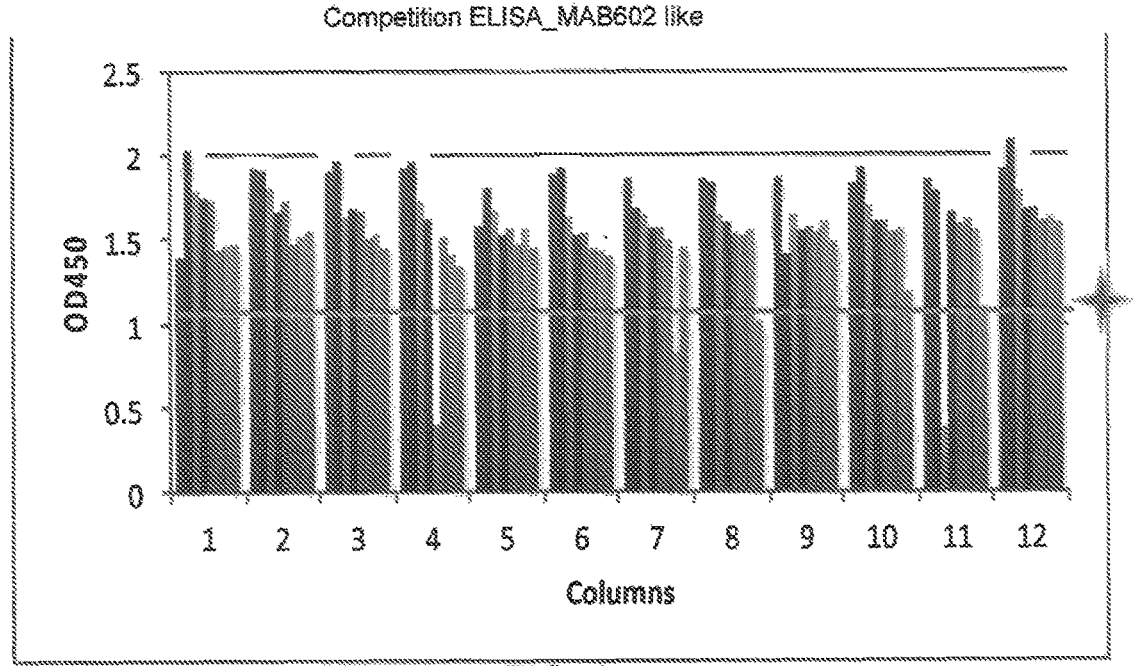
FIG. 2 shows screening of anti-human IL-2 mAbs for binding to presumed specific human IL-2 epitope. Plates were coated with 5344 (a hIL-2 mAb without the herein targeted superagonistic behaviour) and blocked, followed by addition of human IL-2 in order to allow the cytokine to bind to 5344, thus covering a specific epitope of the IL-2. Then the supernatants giving a positive signal in the first screening (see FIG. 1) were added. After allowing the mAbs in the supernatants to bind to the IL-2-5344 complex, a biotinylated MAB602 antibody was added to the plate in order to assess whether the tested mAbs of the supernatants bound to the same (so-called "competitors") or to a different region than MAB602. The competitor mAbs led to an absorbance (OD450) that is two-fold lower than the absorbance obtained with MAB602 alone (in this case OD=1.1, as shown in H11).
Figure 3:
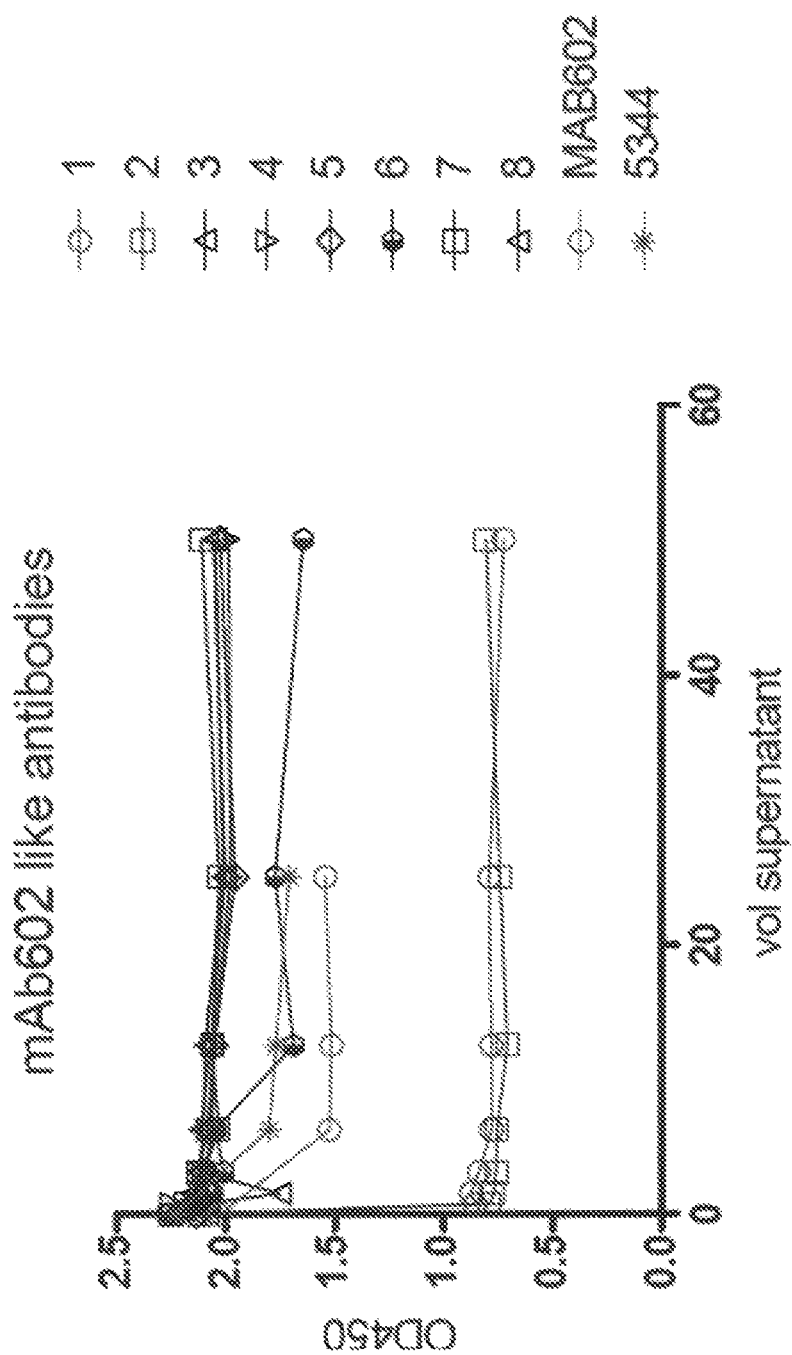
FIG. 3 shows concentration-dependent competition of B cell hybridomas. The supernatants of 8 competitor B cell hybridoma clones of the first screening (see FIG. 2) were expanded and concentrated before use in this assay. The supernatants of these 8 competitor B cell hybridoma clones (labeled 1 to 8) were added in increasing quantities. Competent competitor B cell hybridoma clones reduced the OD450 as much as MAB602 or even more, which is evident for clones 1 and 2. MAB602 at different concentrations (green open circles) served as a control.

The inventors have developed specific screening assays that allow detection of specific antihuman IL-2 antibodies (so-called "binders") in the serum of immunized animals and in the supernatant of the B cell clones obtained after B cell hybridoma fusion. In a second step it was discriminated between standard binders and those targeting a presumed specific epitope of the human IL-2 molecule. One example of such an in vitro enzyme-linked immunosorbent assay (ELISA) performed with different B cell clones, is shown in FIGS. 1 to 3.

Figure 4:
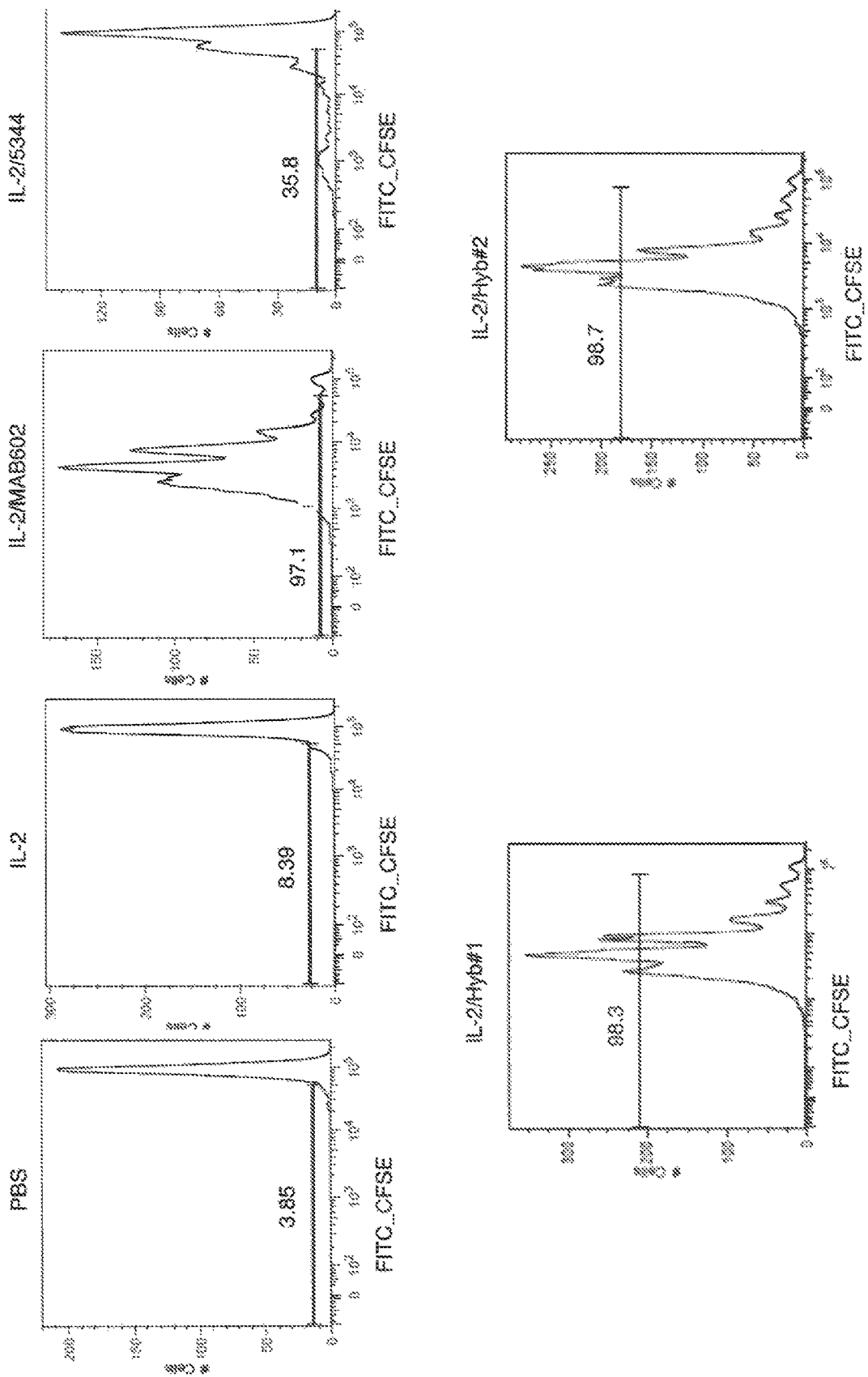
FIG. 4 shows in vivo proliferation of CD8+ T cells. Carboxyfluorescein succinimidyl ester (CFSE)-labeled CD8+ T cells of CD45.1-congenic IL-7 transgenic mice were transferred to CD45.2-congenic WT recipient mice, followed by daily injections of phosphate-buffered saline (PBS), IL-2, IL-2 plus MAB602 (IL-2/MAB602), IL-2 plus 5344 (IL-2/5344), IL-2 plus hybridoma 1 (IL-2/Hyb#1), or IL-2 plus hybridoma 2 (IL-2/Hyb#2) for 4 days. On day 5, lymph nodes and spleens were analyzed for CFSE profiles of donor CD45.1+CD8+ T cells. Shown are the results obtained with the lymph nodes, similar results were obtained in the spleens.
Figure 5A:
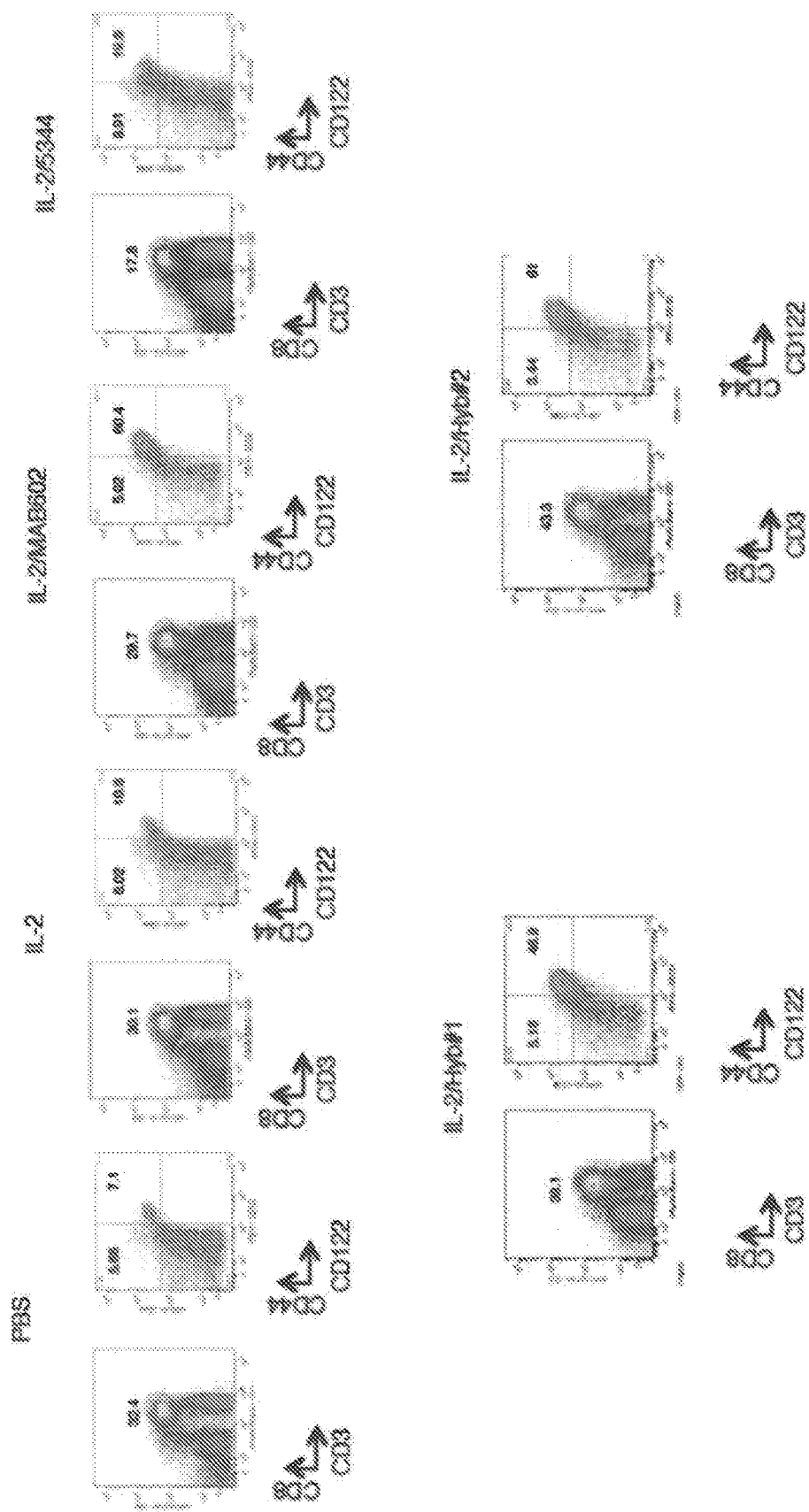
FIG. 5 shows phenotypic characterisation of endogenous CD8+ T cells and NK cells following in vivo treatment using IL-2 plus hybridoma 1 and 2. Mice were treated as in FIG. 4, followed by assessment by flow cytometry of endogenous CD8+ T cell subsets and NK cells in the lymph nodes and spleen. Shown are (A) CD8 vs. CD3 profiles of total lymph node cells (left graphs) and CD44 (activated or memory T cells) vs. CD122 (IL-2 receptor β-subunit, present on activated or memory T cells) profiles of CD3+CD8+ lymph node cells, or (B) NK1.1 vs. CD3 profiles of mice receiving the indicated treatment. Activated/memory CD8+ T cells are high for CD44 and intermediate to high for CD122. NK cells are CD3 negative and NK1.1 positive. Similar results were obtained using spleen cells.
Figure 5B:
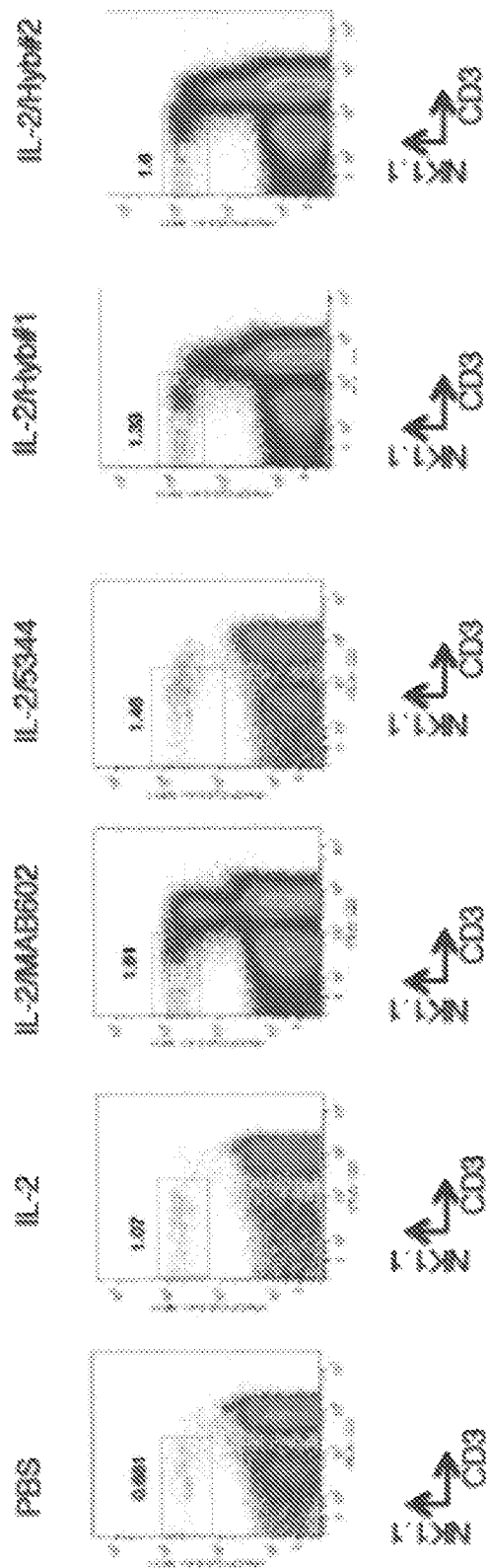
Figure 6A:
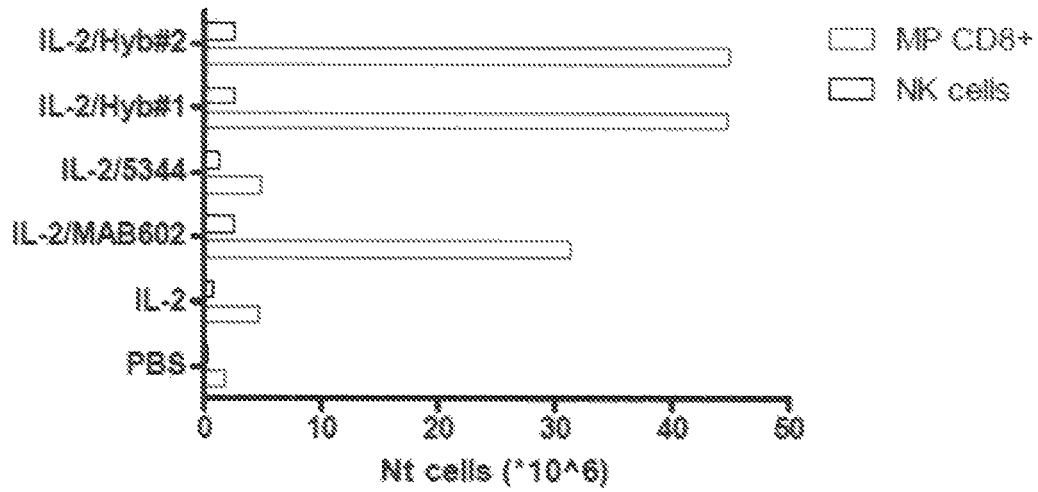
FIG. 6 shows total cell counts of activated/memory CD8+ T cells and NK cells in lymph nodes and spleens. Animals were treated and analyzed as in FIG. 5. Shown are absolute cell counts of CD44high CD8+ T cells (so-called memory cell phenotype, MP CD8+) and of CD3 negative NK1.1+NK cells in lymph nodes (top panel) and spleen (lower panel).
Figure 6B:
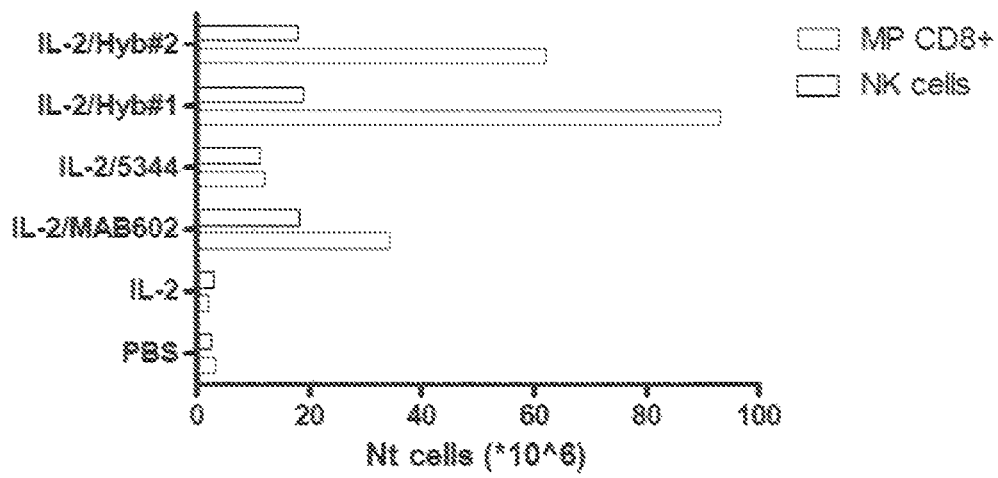

After the in vitro screening of the anti-human IL-2 mAbs, these mAbs were characterised in vivo. To this end and in order to obtain sufficient amounts of mAbs, the mAbs were concentrated from the supernatant of the hybridomas, the amount was estimated using an ELISA and finally the anti-human IL-2 mAbs was tested in mice. The results obtained on proliferation and expansion of CD8$^+$ T cells and NK cells is shown in FIGS. 4 to 6.

Figure 7:
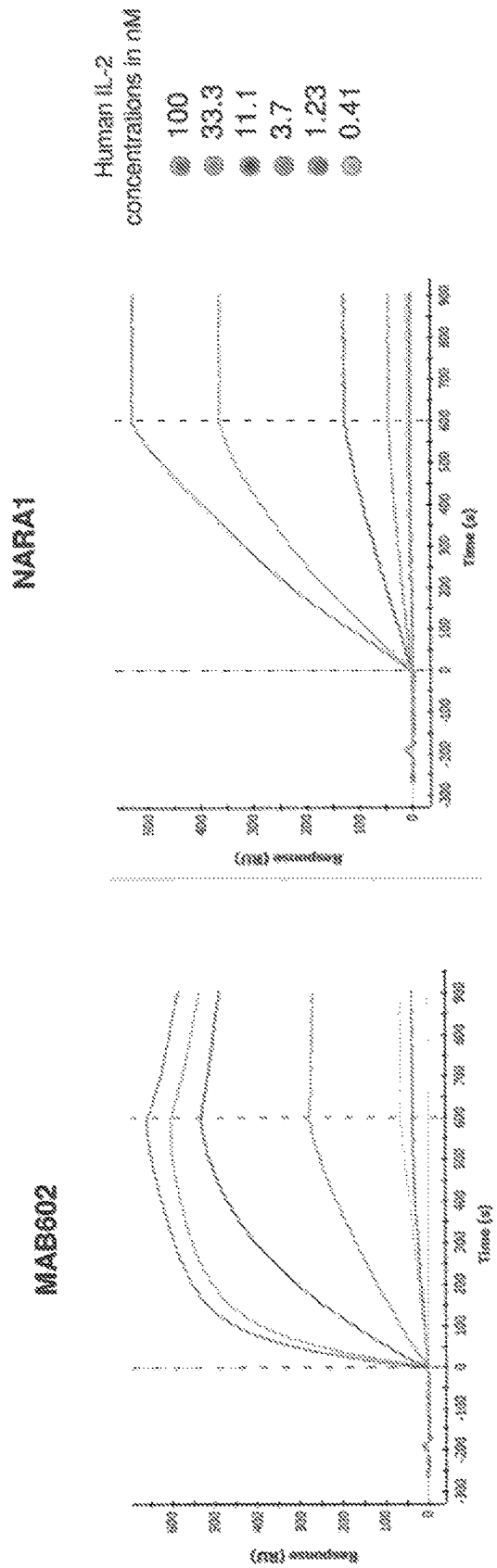
FIG. 7 shows surface plasmon resonance binding curves of the commercially available monoclonal antibody MAB602 (left graph) and the monoclonal antibody NARA1 (right graph), which is the subject of this invention, to human IL-2. For this experiment an amine coupling GLM chip was used. The activation of the carboxylic acid groups in the chip was done using a mix of 1-ethyl-3-3-dimethyl-aminopropyl carbodiimide hydrochlorid (EDC at 0.2 M) and sulfo N-hydroxysulfosuccinimids (s_NHS at 0.05M) at 30 ml/min for 420 seconds (s). The antibodies NARA1 and MAB602 were coated in the chip at 100 mg/ml in a sodium acetate buffer (10 mM pH 4.5). Deactivation was followed adding ethanolamine HCl at 30 ml/min for 300 s. Finally human IL-2 was added at different concentrations (starting from 100 nM and followed by three-fold dilutions) at 100 ml/min, 600 s association, and 240 s dissociation.
Figure 8:
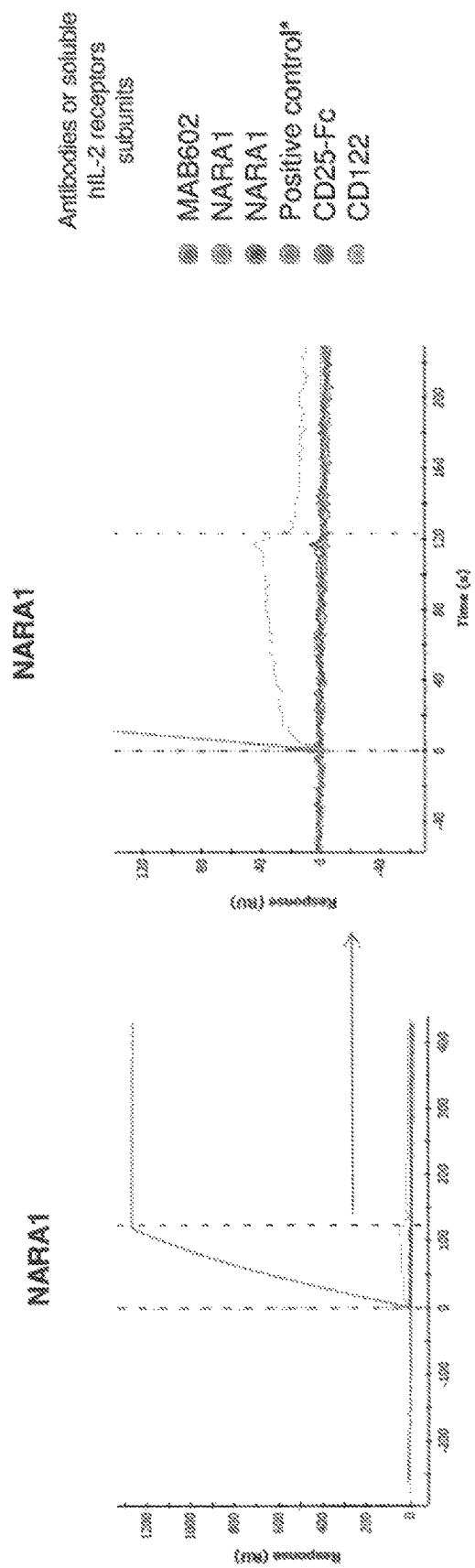
FIG. 8 shows surface plasmon resonance binding curves of human IL-2 bound to the monoclonal antibody NARA1 with the IL-2 receptors subunits CD25 (used here as an Fc fusion of CD25-Fc), CD122, the monoclonal antibody MAB602 or an anti-hIL-2 antibody binding to a different human IL-2 epitope than NARA1 and MAB602. The chip described in FIG. 7 coated with NARA1 and MAB602 was re-used. Regeneration of the chip was done using 10 mM glycine, pH 2.5, 30 ml/min, 60 s. Human IL-2 was added at saturating concentration (1 mM), at 100 ml/min, 120 s association, and 0 s dissociation. Immediately after IL-2 association to the antibodies, the second analytes were added at 100 ml/min, 120 s association, and 240 s dissociation. The concentration used for the cross-binding were: MAB602: 50 nM; NARA1: 50 nM; positive control: 50 nM; CD25-Fc: 500 nM; CD122: 138 nM. When hIL-2 is bound to NARA1, an anti-hIL-2 antibody that recognizes a different hIL-2 epitope (here termed 'positive control') binds strongly to the hIL-2/NARA1 complex as expected (green line in FIG. 8). Alternatively, IL-2Ra (in the form of CD25-Fc) cannot bind to hIL-2 when hIL-2 is already bound to NARA1 (pink line, FIG. 8), however, IL-2Rβ (CD122) still binds to hIL-2 when hIL-2 is already bound to NARA1 (orange line, FIG. 8).
Figure 9:
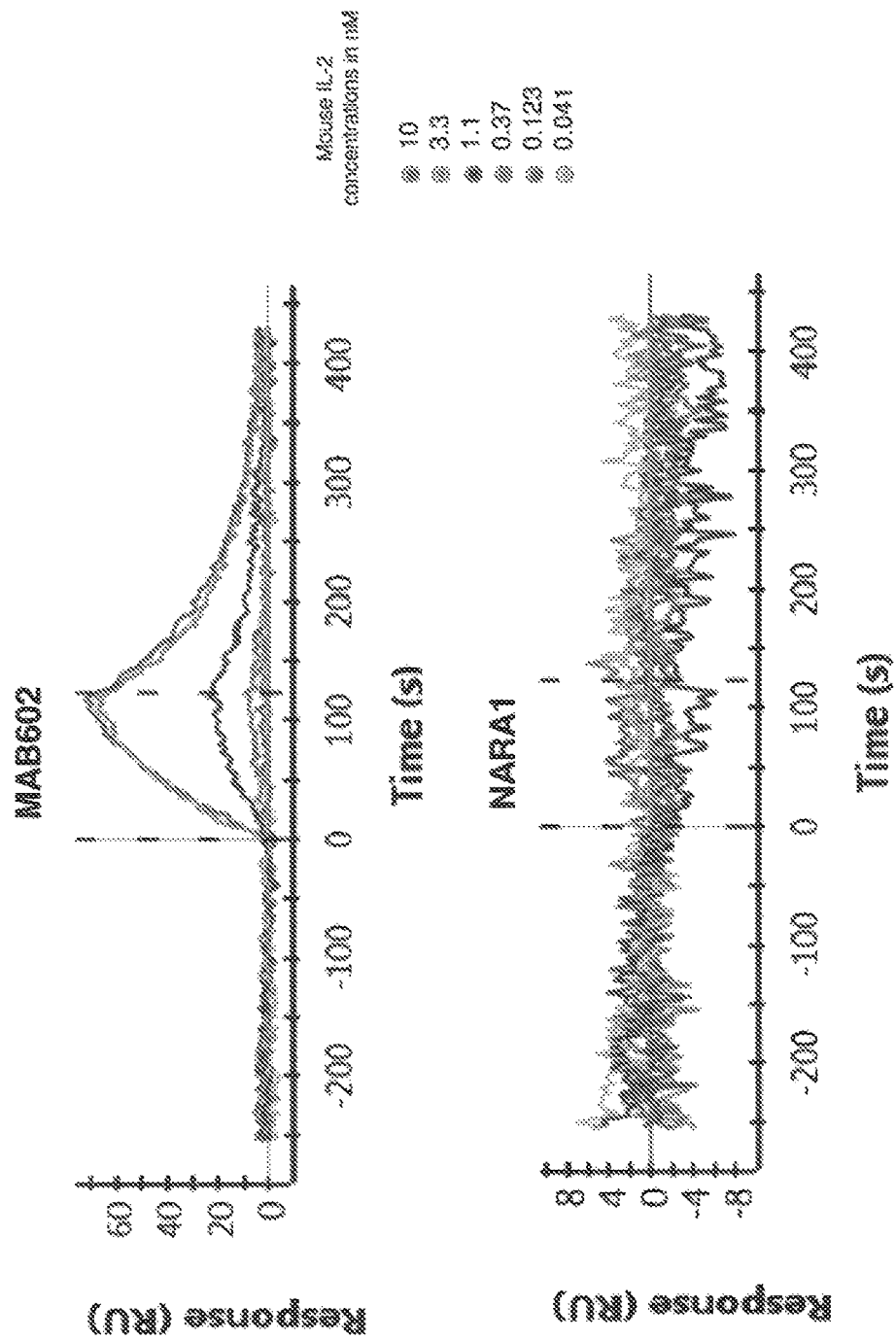
FIG. 9 shows surface plasmon resonance binding curves of the monoclonal antibodies MAB602 (top graph) and NARA1 (lower graph) to murine IL-2. The same chip used for the generation of the data in FIGS. 7 and 8 was re-used. Regeneration of the chip was done with 10 mM glycine, pH 2.5, 30 ml/min, 60 s. Mouse IL-2 (mIL-2) or human IL-2 (hIL-2) starting at 10 nM and then doing a three-fold dilution was injected at 100 ml/min, 120 s association, 5 and 240 s dissociation. In the top graph MAB602 shows cross-reactivity by binding to mouse IL-2. Especially, with higher concentrations of murine interleukin-2 (>1 nM) the binding curves differ significantly from background levels with response units 10 (RU) well above 10. Whereas NARA1 (lower graph) displays no measurable cross-reactivity to murine IL-2 at all concentrations tested.

In order to characterize the binding properties of the anti-human IL-2 mAbs the binding to human interleukin-2 was tested with surface plasmon resonance binding assays. The commercially available anti-human IL-2 mAb MAB602 was measured as a comparison. In FIG. 7 binding curves of MAB602 (left graph) and NARA1 (an antibody according to this invention; right graph) to human interleukin-2 at varying concentrations are shown. The dissociation constant ($K_D$) as well as the rate constants $K_{on}$ and $K_{off}$ measured for MAB602 and NARA1 are shown in Table 1.

TABLE 1

Table 1: Binding properties of anti-human IL-2 mAbs to human IL-2

|  | $K_{on}$ (M*s$^{-1}$) | $K_{off}$ (s$^{-1}$) | $K_D$ (nM) |
| --- | --- | --- | --- |
| MAB602 | 5.8 × 10$^4$ | 4.94 × 10$^{-4}$ | 9.7 |
| NARA1 | 1.78 × 10$^4$ | 2.08 × 10$^{-5}$ | 1.2 |

Examples

Antibodies of the invention include the antibody NARA1, which was derived, isolated and structurally characterized by its full length heavy chain according to SEQ ID NO: 5 and its full length light chain amino acid sequences according to SEQ ID NO: 6.

The corresponding variable regions, $V_H$ and $V_L$ amino acid sequences of NARA1 are. SEQ ID NO: 19 (variable heavy) and SEQ ID NO: 20 (variable light).

Full length light and heavy chains nucleotide coding sequences of NARA1 are SEQ ID NO: 3 (heavy chain coding sequence, including leader sequence) and SEQ ID NO: 4 (light chain coding sequence, including leader sequence).

Variable light and heavy chains nucleotide coding sequences of NARA1 are SEQ ID NO: 21 (variable heavy coding sequence) and SEQ ID NO: 22 (variable light coding sequence).

The CDR regions of NARA1 are delineated using the Kabat system (Kabat, E. A., et al. 1991, Sequences of Proteins of Immunological Interest, Fifth Edition, U.S. Department of Health and Human Services, NIH Publication No. 91-3242, see also Zhao&Lu 2009, Molecular Immunology 47:694-700). For the ease of reading, when CDR regions are delineated according to Kabat definition, they are called hereafter HCDR1, HCDR2, HCDR3, LCDR1, LCDR2, LCDR3 respectively. The CDR regions of NARA1 are: HCDR1 according to SEQ ID NO: 7, HCDR2 according to SEQ ID NO: 8, HCDR3 according to SEQ ID NO: 9, LCDR1 according to SEQ ID NO: 10, LCDR2 according to SEQ ID NO: 11, LCDR3 according to SEQ ID NO: 12.

Nucleotide coding sequences for the CDR regions of NARA1 are: HCDR1 coding sequence according to SEQ ID NO: 13, HCDR2 coding sequence according to SEQ ID NO: 14, HCDR3 coding sequence according to SEQ ID NO: 15, LCDR1 coding sequence according to SEQ ID NO: 16, LCDR2 coding sequence according to SEQ ID NO: 17, LCDR3 coding sequence according to SEQ ID NO: 18.

Fusion proteins are also provided according to SEQ ID NO: 23 and SEQ ID NO: 24. SEQ ID NO: 23 is a fusion protein comprising the variable heavy chain of NARA1 with its N-terminus fused to the C-terminus of hIL-2 via a GxS linker. SEQ ID NO: 24 is a fusion protein comprising the variable light chain of NARA1 with its N-terminus fused to the C-terminus of hIL-2 via a GxS linker.

(a) Example 1. Crystal Structure of NARA1

(i) Material and Methods

The complex structure of a human Interleukin 2 mutant (SEQ ID NO:2), called "Proleukin", bound to the Fab fragment of antibody "NARA 1" (SEQ ID NO: 5 and 6) was determined. The resulting numbering of residues on Proleukin is given according to the numbering of wt IL-2.

As will be discussed in detail below, the differences in sequence between Proleukin and wt hIL-2 are irrelevant and Proleukin is a valid model for structural analysis of hIL-2.

To define the epitope, X-ray crystallography was used to solve the atomic-resolution structure of the complex mentioned above. X-ray crystallography is a technology that has become routinely and widely used to generate structural data for biomolecules including antibodies and their complexes with antigens (Adms et al, (2013) Annual Review Biophysics 42:265-287; Garman, (2014) Science 343:1102-1108; Joachimiak, (2009) Current Opinio Structural Biology 19:573-584.)

The antigen, Proleukin, is commercially available as lyophilyzed powder together with excipients (every 1 mg Proleukin is mixed with approximately 50 mg mannitol, 0.18 mg sodium dodecyl sulfate, 0.173 mg sodium dihydrogen phosphate, and 0.89 mg disodium hydrogen phosphate). Before used for complex formation, Proleukin was purified by reverse-phase HPLC to remove the excipients.

The Fab fragment of NARA1 (NARA1-Fab) was generated by papain cleavage of the full-length antibody followed by Protein A chromatography. Briefly, 6.5 ml full-length NARA1 (9 mg/ml in 50 mM citrate buffer with 90 mM sodium chloride at pH 7.0) was mixed with 5 mM DTT and 590 ug Papain (Roche). The cleavage reaction was kept at room temperature for 16 h and stopped by addition of 15 ul 56 mM E64 solution (Roche). The cleavage solution was then diluted 10 times with 25 mM Tris, 25 mM NaCl, pH 8.0 and loaded onto a 5 ml Protein A column (GE Healthcare) equilibrate with 5 column volume of 25 mM Tris, 25 mM NaCl, pH 8.0 and Fab fragment was in the loading-through fraction and Fc fragment was bound to the Protein A column.

To form complex, Proleukin powder after HPLC was dissolved in $H_2O$ at the concentration of 5.5 mg/ml. 6.6 mg Proleukin, in excess, was added to 11.5 mg NARA1 Fab fragment solution drop by drop. Centrifugation was used to remove the excess Proleukin that was precipitated under current condition. The complex was then purified by gel filtration with Superdex 200 10×300 (GE Healthcare) with running buffer of 25 mM Tris, 25 mM NaCl, pH 7.4.

Proleukin/NARA1-Fab complex after gel filtration was concentrated to 14 mg/ml and was screened by vapour diffusion method as sitting drops. The protein solution was mixed 1:1 with reservoir buffer to a total size of 0.4 ul. The experiments were set up with Phoenix robotic system (Art Robbins Instruments), stored in a RockImager hotel (Formulatrix) at 19° C., and imaged automatically. Crystals were harvested 4 days after screening under condition of 20% w/v polyethylene Glycol 3350 and 0.2M sodium nitrate. Crystals were cryo-protected with reservoir buffer containing 10% glycerol and flashed frozen in liquid nitrogen prior to data collection. Diffraction data were collected at the Swiss Light Source (Villigen, Switzerland) at beam-line PX-II with a Pilatus pixel detector using x-ray radiation wavelength of 0.99998 Å.

The dataset was processed with XDS and XSCALE (version Dec. 6, 2010) and the structure was resolved with molecular replacement method with the program PHASERby using Protein Data Bank entry "3INK" as search model for IL-2 and Protein Data Bank entry "3TTT" as search model for Fab fragment. Iterative model building and refinement were performed with the programs Coot (Crystallographic Object-Oriented Toolkit) and AUTOBUSTER (Bricogne et al., 2011). All figures were generated with the program PyMOL (Moelcular Graphics Systems; Delano Scientific: Palo Alto, Calif.; www.pymol.org).

Epitope residues are defined as those residues from Proleukin that are within 4 Å distance from any atom in Fab fragment of NARA1 and are further confirmed by CCP4 program CONTACT and AREAIMOL (Collaborative Computational Project, Number 4, version 6.4.0). Similarly paratope residues are defined as those residues from NARA1-Fab that are within 4 Å distance from any atom in Proleukin.

(ii) Results

The Proleukin/NARA1-Fab complex was solved to 1.95 Å in space group C 1 2 1 with unit cell dimension a=201.8 Å, b=36.2 Å, c=88.7 Å, alpha=90°, beta=102.9°, gamma=90°. Please refer to Table 2 for detailed structure statistics. In each asymmetric unit, there is one complex molecule.

TABLE 2

Structure statistics for Proleukin/NARA1-Fab complex

| Data collection | |
|---|---|
| Space group | C1 2 1 |
| Cell dimensions | |
| a, b, c (Å) | 201.757, 36.233, 88.707 |
| a, b, g (°) | 90, 102.93, 90 |
| Resolution (Å) | 58.74-1.95 |
| $R_{merge}$ | 0.066 (0.472) |
| I |σ| | 14.18 (2.59) |
| Completeness (%) | 84.8 (96) |
| Redundancy | 3.19 |
| Refinement | |
| Resolution (Å) | 58.74-1.95 |
| No. reflections | 34750 |
| $R_{work}/R_{free}$ | 0.2052/0.2872 |
| Ramachandran plot | |
| Outliners | 0.0162 |
| Allowed | 0.0378 |
| Favored | 0.9459 |
| R.m.s. deviations | |
| Bond lengths (Å) | 0.01 |
| Bond angles (°) | 1.7 |

1) Epitope and Paratope Analysis

Figure 10:
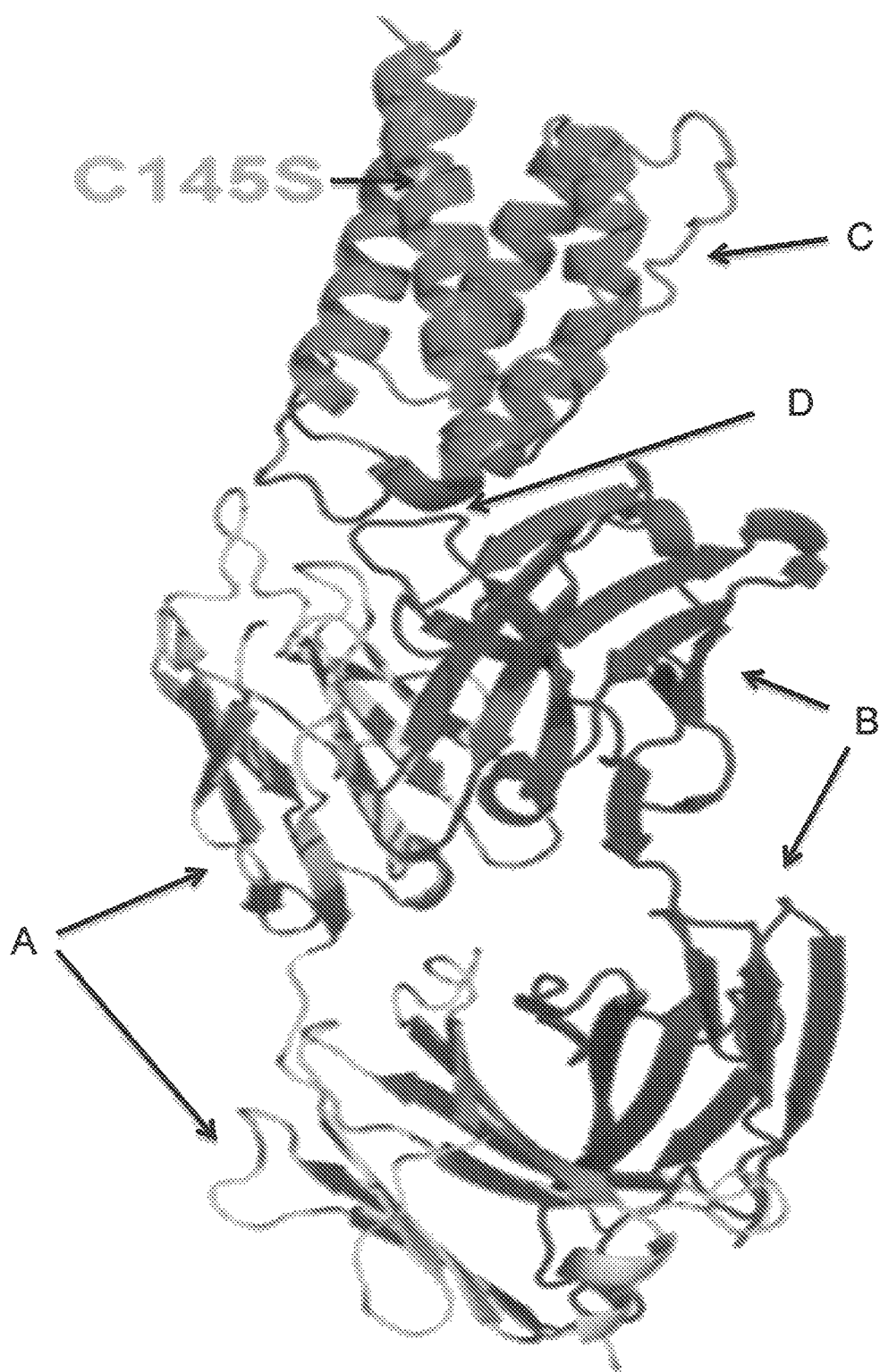
FIG. 10 provides the overview of the three-dimension structure of Proleukin/Fab-NARA1 complex as obtained in Example 1.

FIG. 10 provides the overview of the three-dimension structure of Proleukin/Fab-NARA1 complex as obtained in Example 1. Light chain of Fab fragment of NARA1 is designated A, heavy chain of Fab fragment of NARA1 is shown as B, epitope residues recognized by NARA1-Fab are designated D, and Proleukin is designated C and the mutation, C145S, is highlighted.

Figure 11:
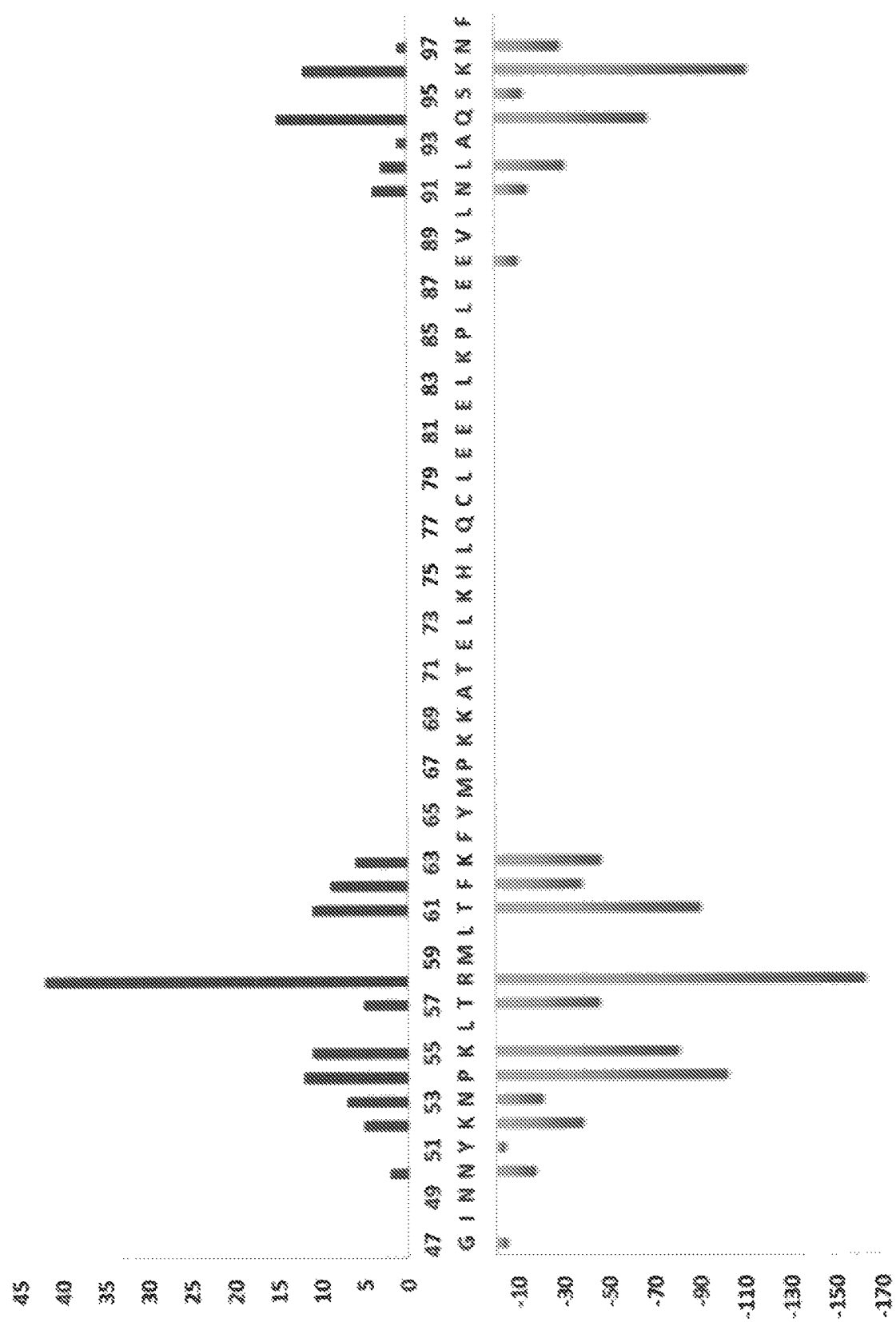
FIG. 11 provides further analysis of epitope residues. The X-axis lists the amino acid sequence and numbering according to SEQ ID No 1. The upper side of Y-axis shows the total number of atoms of NARA1-Fab that are within 4 Å from corresponding residue from Proleukin and the lower side of Y-axis shows the reduced solvent-accessible area (Å$^2$) of corresponding residue from Proleukin as a consequence of binding to NARA1-Fab.

FIG. 11 provides further analysis of epitope residues. The X-axis lists the amino acid sequence and numbering according to SEQ ID No 1. The upper side of Y-axis demonstrates the total number of atoms of NARA1-Fab that are within 4 Å from corresponding residue from Proleukin and the lower side of Y-axis demonstrates the reduced solvent-accessible area ($Å^2$) after binding to NARA1-Fab.

Proleukin used in Example 1 contains mutation of C145S. As shown in FIG. 10, C145S is far away from the epitope region. In addition the superposition of Cα atoms between Proleukin in Example 1 with Cα atoms from wt hIL-2 in complex with CD25, CD122, and CD132 (PDB: 2B5I) shows r.m.s.d of 0.447 Å, which indicates that the mutation does not disturb the over-all structure. Hence Proleukin with C145S mutation is a valid model for structural analysis for wt hIL-2.

hIL-2 is 4-helix bundle protein and the 4 helices are named from N-terminus to C-terminus as A, B, C, and D, respectively. The epitope recognized by NARA1-Fab as shown in FIG. 10 is a conformational epitope and spans two regions as shown in FIG. 11: one region (N50-K63) comprises a loop and a short helix and connects helix A and B, and the other region (N91-N97) comprises a loop and connects helix B and C.

Figure 12:
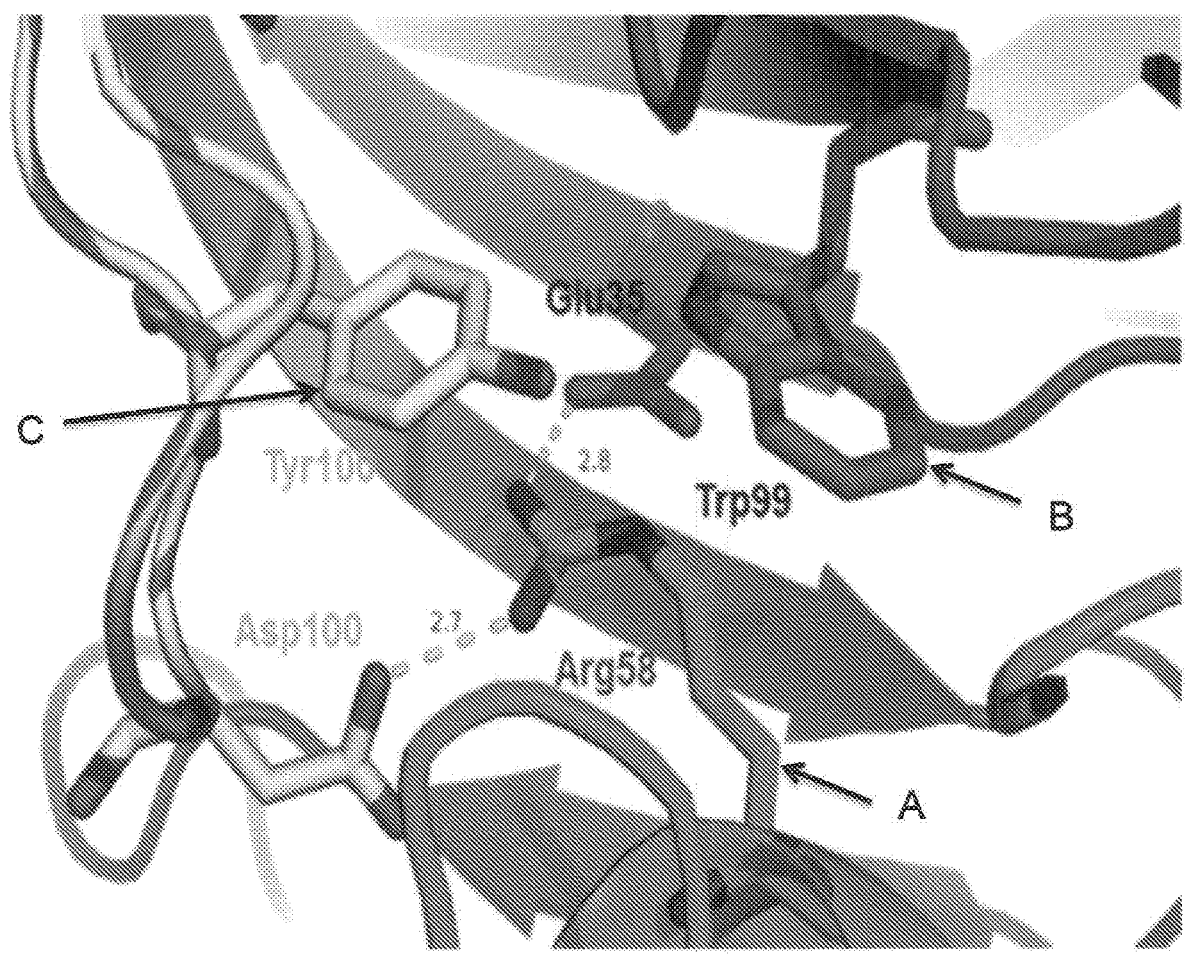
FIG. 12 illustrates the most critical epitope residue recognized by the NARA1-Fab.

The epitope residues together with interacting paratope residues from NARA1-Fab are summarized in Table 3. Among all the epitope residues, Arg58 as shown in FIG. 11 is the most critical epitope residue for binding with NARA1-Fab, as this residue alone has 42 interacting atoms from NARA1-Fab and accounts for 17.7% of total reduced solvent-accessible surface area as a consequence of binding to NARA1-Fab. Furthermore Arg58, as shown in FIG. 12, forms two strong salt-bridges with Glu35 in HCDR1 and with Asp100 from LCDR3, respectively. Arg58 also makes π-action interaction with the aromatic ring of Try100 from LCDR3. Residues K52, P54, K55, T57, T61, F62, K63, Q94, and K96 are also considered important for the binding to NARA1-Fab, since they all show equal to/more than 5 interacting atoms from NARA1-Fab and larger than 30 $Å^2$ reduced solvent-accessible area as shown in FIG. 11.

TABLE 3

Epitope and paratope summary

| Light chain residue | Epitope residue | Heavy chain residue |
| --- | --- | --- |
| Y31 | N50 | |
| Y31 | K52 | |
| Y31 | N53 | |
| Y31, Y36, S95, N96 | P54 | |
| | K55 | W99, G101, G103, Y105 |
| D98 | T57 | |
| D98, Y100 | R58 | L33, E35, W47, W99 |
| | T61 | N52, S55, N59 |
| | F62 | L33, N52 |
| | K63 | S55 |
| | N91 | G101, D102, G103 |
| | L92 | W99, G101 |
| | A93 | G101 |
| | Q94 | D102, G103, Y104 |
| D32, D34 | K96 | Y104 |
| D32 | N97 | |

FIG. 12 illustrates Arg58 as the most critical epitope residue recognized the NARA1-Fab. A represents Proleukin, B represents heavy chain, and C represents light chain. The involved residues are shown as sticks.

2) NARA1-Fab Binding Properties

Figure 13:
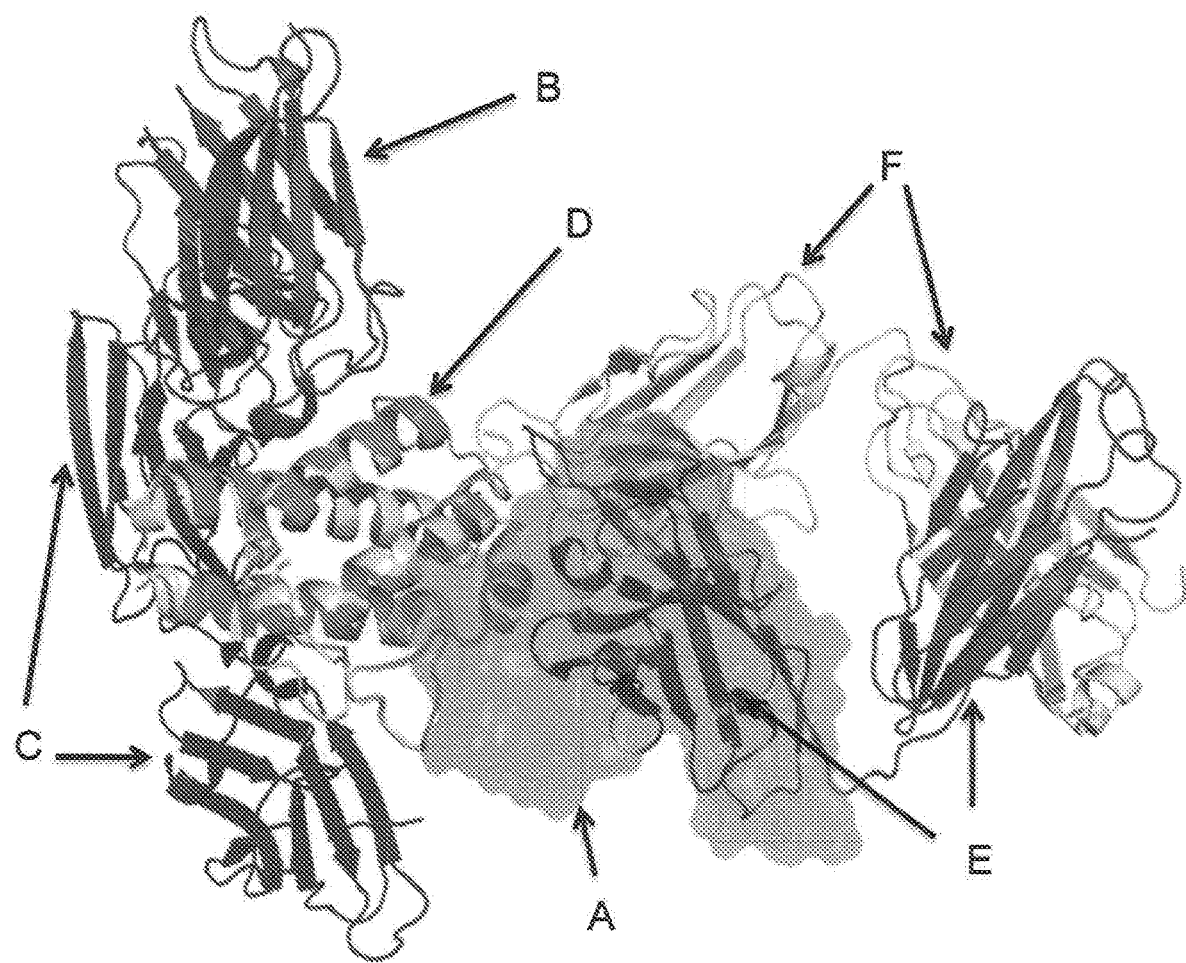
FIG. 13 shows the overlay of Proleukin/NARA1-Fab complex with IL-2/CD25/CD122/CD132 quaternary complex.

FIG. 13 shows the overlay of Proleukin/NARA1-Fab complex with IL-2/CD25/CD122/CD132 quaternary complex. The quaternary complex structure comes from PDB entry "2B5I" with cartoon D in pale cyan representing wt hIL-2, cartoon B in red representing CD122, cartoon C in blue representing CD132, and surface A in green representing CD25. In the Proleukin/NARA1-Fab complex structure, cyan cartoon D overlayed with wt hIL-2 represents Proleukin, cartoon E in magenta represents heavy chain, and cartoon F in yellow represents the light chain.

The structure overlay of the two complexes as shown in FIG. 13 clearly shows that NARA1-Fab forms direct competition against CD25 but not against CD122/CD132, which is consistent with the observation that IL-2/NARA1 complex demonstrates mainly pro-T effector cell activity rather than pro-Treg activity.

Figure 14:
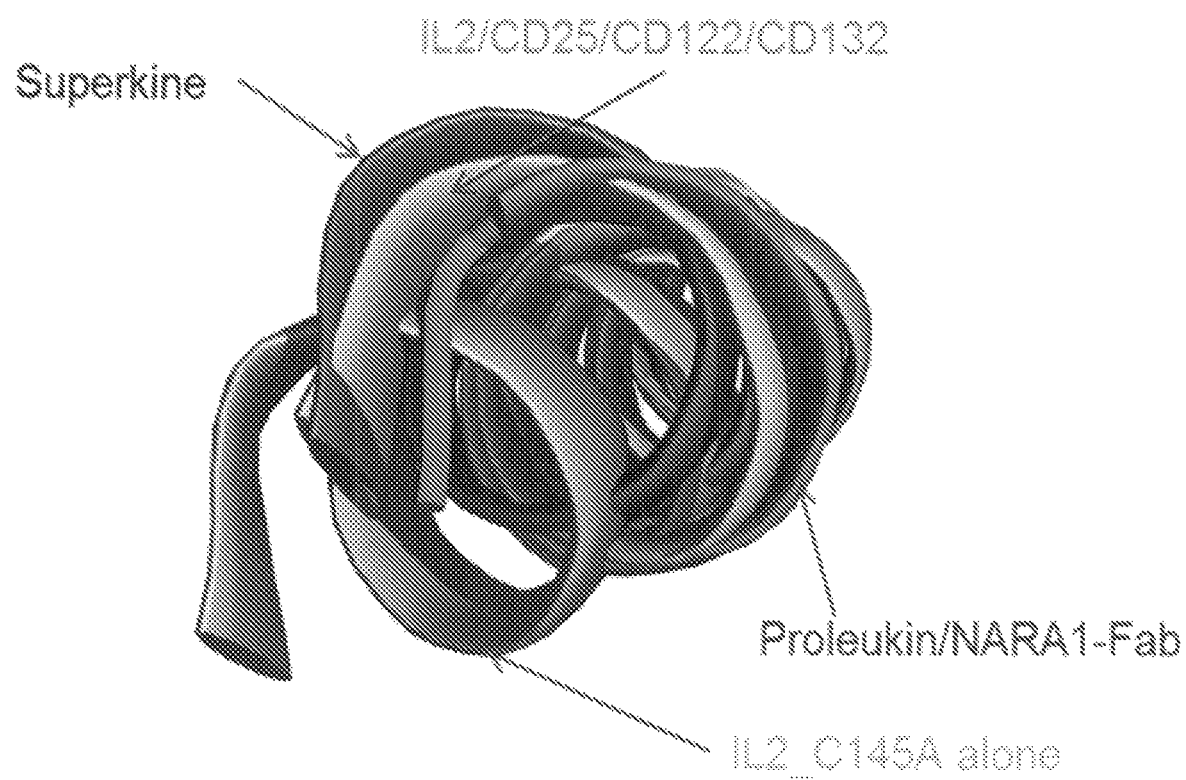
FIG. 14 displays the overlay of C helices from IL-2_C145A (PDB: 3INK), Superkine (PDB: 3QB1), IL-2/CD25/CD122/CD132 (PDB: 2B5I), and Proleukin/NARA1-Fab.

3) C Helix of Proleukin in Complex with NARA1-Fab Adopts Conformation that is Similar to that in Quaternary Complex FIG. 14 displays the overlay of C helices from IL-2_C145A (PDB: 3INK), Superkine (PDB: 3QB1), IL-2/CD25/CD122/CD132 (PDB: 2B5I), and Proleukin/NARA1-Fab.

The polar interface between helix C in IL-2 and CD122 plays an important role in binding between the two parts (Wang et al (2005) Science 310:1159-1163). In 2012 Levin, et al have demonstrated that superkine, an IL-2 mutant, alone has a Helix C adopting confirmation similar to that in the quaternary complex and superkine showed ~215 times higher binding affinity towards CD122 than wtIL-2 (Levin et al, (2012) Nature 484:529-533). It was observed that such a conformational change in helix C is associated with conformational stabilization, which then reduces the energetic penalties for binding to CD122. As shown in FIG. 14, The conformation of helix C from Proleukin in complex with NARA1-Fab is also similar to that observed in Superkine as well as in IL-2/CD25/CD122/CD132 quaternary complex, therefore it is possible that Proleukin/NARA1-Fab complex may demonstrate higher binding affinity towards CD122 than wt hIL-2 does.

(b) Example 2. Linear Peptide Mapping of NARA1 and MAB602

In order to map the epitope of the NARA1 and MAB602 antibodies, a first library of 15-mer peptides was generated based on the sequence of human IL2. A second library of selected 15-mer peptides was also generated based on the mutation of 3 specific residues F(62), Y(65) and L(92). The latter mutations were done based on the Roche/Glycart IL2 mutein, as disclosed in WO2012/107417A1 which has these 3 mutations. Previous work done in lab Boyman (unpublished) showed that the commercial mouse anti-human IL2 mAb 602 with analogous function as A1 has strongly reduced binding to the F42A mutant of IL2 (one of the IL2 docking sites to CD25).

(i) Material and Methods

Accordingly, each peptide in the first library has 15 amino acids and the sequence is derived by scanning the sequence of interest (see Table 4, reference peptides 1 to 41) with a step of 3 residues, starting from the N-terminus. Therefore a ladder is generated and each peptide contains 12 overlapping residues with the previous peptide and 12 overlapping residues with the following peptide in the ladder. In total, 41 peptides were generated from the expressed human IL2 sequence.

A second library of peptides was generated by mutating F(62), Y(65) and L(92) to alanine in all corresponding peptides in the first library generated as described above (see Table 4, reference peptides no 42 to 60).

For both libraries, the parental cysteines have been replaced by a serine (underlined residues) to avoid unspecific binding.

TABLE 4

Library of reference peptides

| Reference Peptide No. | Sequence Residue in bold are the Alanine (A) replacing specific residues. Residue are the serine (S) replacing cysteines (C) | SEQ ID NO: |
|---|---|---|
| 1 | APTSSSTKKTQLQLE | 25 |
| 2 | SSSTKKTQLQLEHLL | 26 |
| 3 | TKKTQLQLEHLLLDL | 27 |
| 4 | TQLQLEHLLLDLQMI | 28 |
| 5 | QLEHLLLDLQMILNG | 29 |
| 6 | HLLLDLQMILNGINN | 30 |
| 7 | LDLQMILNGINNYKN | 31 |
| 8 | QMILNGINNYKNPKL | 32 |
| 9 | LNGINNYKNPKLTRM | 33 |
| 10 | INNYKNPKLTRMLTF | 34 |
| 11 | YKNPKLTRMLTFKFY | 35 |
| 12 | PKLTRMLTFKFYMPK | 36 |
| 13 | TRMLTFKFYMPKKAT | 37 |
| 14 | LTFKFYMPKKATELK | 38 |
| 15 | KFYMPKKATELKHLQ | 39 |
| 16 | MPKKATELKHLQSLE | 40 |
| 17 | KATELKHLQSLEEEL | 41 |
| 18 | ELKHLQSLEEELKPL | 42 |
| 19 | HLQSLEEELKPLEEV | 43 |
| 20 | SLEEELKPLEEVLNL | 44 |
| 21 | EELKPLEEVLNLAQS | 45 |
| 22 | KPLEEVLNLAQSKNF | 46 |

TABLE 4-continued

Library of reference peptides

| Reference Peptide No. | Sequence Residue in bold are the Alanine (A) replacing specific residues. Residue are the serine (S) replacing cysteines (C) | SEQ ID NO: |
|---|---|---|
| 23 | EEVLNLAQSKNFHLR | 47 |
| 24 | LNLAQSKNFHLRPRD | 48 |
| 25 | AQSKNFHLRPRDLIS | 49 |
| 26 | KNFHLRPRDLISNIN | 50 |
| 27 | HLRPRDLISNINVIV | 51 |
| 28 | PRDLISNINVIVLEL | 52 |
| 29 | LISNINVIVLELKGS | 53 |
| 30 | NINVIVLELKGSETT | 54 |
| 31 | VIVLELKGSETTFMS | 55 |
| 32 | LELKGSETTFMSEYA | 56 |
| 33 | KGSETTFMSEYADET | 57 |
| 34 | ETTFMSEYADETATI | 58 |
| 35 | FMSEYADETATIVEF | 59 |
| 36 | EYADETATIVEFLNR | 60 |
| 37 | DETATIVEFLNRWIT | 61 |
| 38 | ATIVEFLNRWITFSQ | 62 |
| 39 | VEFLNRWITFSQSII | 63 |
| 40 | LNRWITFSQSIISTL | 64 |
| 41 | NRWITFSQSIISTLT | 65 |
| 42 | INNYKNPKLTRMLTA | 66 |
| 43 | YKNPKLTRMLTAKFY | 67 |
| 47 | YKNPKLTRMLTFKFA | 68 |
| 52 | YKNPKLTRMLTAKFA | 69 |
| 44 | PKLTRMLTAKFYMPK | 70 |
| 48 | PKLTRMLTFKFAMPK | 71 |
| 53 | PKLTRMLTAKFAMPK | 72 |
| 45 | TRMLTAKFYMPKKAT | 73 |
| 49 | TRMLTFKFAMPKKAT | 74 |
| 54 | TRMLTAKFAMPKKAT | 75 |
| 46 | LTAKFYMPKKATELK | 76 |
| 50 | LTFKFAMPKKATELK | 77 |
| 55 | LTAKFAMPKKATELK | 78 |
| 51 | KFAMPKKATELKHLQ | 79 |
| 56 | SLEEELKPLEEVLNA | 80 |

TABLE 4-continued

Library of reference peptides

| Reference Peptide No. | Sequence Residue in bold are the Alanine (A) replacing specific residues. Residue are the serine (S) replacing cysteines (C) | SEQ ID NO: |
|---|---|---|
| 57 | EELKPLEEVLNAAQS | 81 |
| 58 | KPLEEVLNAAQSKNF | 82 |
| 59 | EEVLNAAQSKNFHLR | 83 |
| 60 | ANLAQSKNFHLRPRD | 84 |

Both set of peptides were printed on microarray slides in triplicate, incubated with the antibodies of interest (MAb602 and NARA1) and control antibodies. Additional incubations are with unrelated antibodies from the same isotype (mouse control IgG2a/lambda and mouse control IgG2a/kappa), and secondary antibodies (anti-mouse IgG (Thermo 84545, label DL650) or anti-mouse IgG (JIR 115-175-072, Label Cy5)) to assess unspecific binding due to the detection antibody.

The experiments are performed essentially as described in Maksimov P, et al. 2012, PLoS One 7:e34212. doi:10.1371/journal. pone. 0034212.

The determination of peptide-antibody binding was performed by RepliTope-analysis where the peptide microarray (triplicate) was incubated with the primary antibody followed by a fluorescently labelled secondary antibody directed against the Fc-part of the primary one. All steps were performed on a TECAN microarray processing station enabling highly reliable and reproducible washing and incubation steps. After performing the incubation steps and subsequent to the final washing steps (to remove the unbound secondary antibodies) the microarrays were dried using a nitrogen stream and scanned in a high resolution microarray scanning system with appropriate wavelength settings. Control incubations were performed with an unrelated antibody having the same isotype to exclude false positive signals.

The resulting images were analyzed und quantified using spot-recognition software GenePix (Molecular Devices). For each spot, the mean signal intensity was extracted (between 0 and 65535 arbitrary units). For further data evaluation, the MMC2 values were determined. The MMC2 equals the mean value of all three instances on the microarray. Except the coefficient of variation (CV)—standard-deviation divided by the mean value—is larger 0.5, in this case the mean of the two closest values (MC2) is assigned to MMC2.

(ii) Results

The data are summarized in Table 5.

The anti-IL2 (NARA1) antibody did not show any significant reactivity towards the immobilized peptides. Only peptide 10 exhibited a weak response, however, this peptide was also weakly recognized by the mouse control antibodies.

The commercial antibody MAB602 (mIgG2a) provided some weak signals on peptide 22 to 26 and some strong for peptides 10 to 13.

TABLE 5

Result of Linear Epitope Mapping

| Reference peptide no. | Sequence | Signal intensity for MAB602 after subtraction of control signal (AU) | Signal intensity for NARA1 after subtraction of control signal (AU) | SEQ ID NO: |
|---|---|---|---|---|
| 10 | INNYKNPKLTRMLTF | 45954 | 20883 | 34 |
| 11 | YKNPKLTRMLTFKFY | 49726 | 1189 | 35 |
| 12 | PKLTRMLTFKFYMPK | 28849 | 1127 | 36 |
| 13 | TRMLTFKFYMPKKAT | 5250 | 224 | 37 |
| 22 | KPLEEVLNLAQSKNF | 4998 | 0 | 46 |
| 23 | EEVLNLAQSKNFHLR | 13287 | 32 | 47 |
| 24 | LNLAQSKNFHLRPRD | 3289 | 282 | 48 |
| 25 | AQSKNFHLRPRDLIS | 5220 | 0 | 49 |
| 26 | KNFHLRPRDLISNIN | 7509 | 0 | 50 |

The overlapping sequences within both set of peptides are considered as containing the binding amino acid to the target antibody (Table 5). One stretch is a strong binder to MAB602 whereas the other is rather a weak binder to MAB602:

Strong: (57) TRMLTF (62) (amino acids 57-62 of SEQ ID NO:24)

Weaker: (96) KNF (98)

Ala mutation on specific residues F42(62), Y45(65), L72 (92) showed that residue F42(62) is clearly an important residue for the binding to antibody MAB602 (Table 6).

TABLE 6

Mutagenesis characterization

| Reference peptide no. | Sequence Residue in bold are the Alanine (A) which are replacing specific residues | Signal intensity for MAB602 after subtraction of control signal (AU) | Signal intensity for NARA1 after subtraction of control signal (AU) | SEQ ID NO: |
|---|---|---|---|---|
| 10 | INNYKNPKLTRMLTF | 45954 | 20883 | 34 |
| 42 | INNYKNPKLTRMLTA | 246 | 162 | 66 |
| 11 | YKNPKLTRMLTFKFY | 49726 | 1189 | 35 |
| 43 | YKNPKLTRMLTAKFY | 42784 | 507 | 67 |
| 47 | YKNPKLTRMLTFKFA | 21382 | 251 | 68 |
| 52 | YKNPKLTRMLTAKFA | 13089 | 238 | 69 |
| 12 | PKLTRMLTFKFYMPK | 28849 | 1127 | 36 |
| 44 | PKLTRMLTAKFYMPK | 5027 | 432 | 70 |
| 48 | PKLTRMLTFKFAMPK | 13394 | 6205 | 71 |
| 53 | PKLTRMLTAKFAMPK | 0 | 24 | 72 |
| 13 | TRMLTFKFYMPKKAT | 5250 | 224 | 37 |
| 45 | TRMLTAKFYMPKKAT | 0 | 0 | 73 |
| 49 | TRMLTFKFAMPKKAT | 3018 | 1492 | 74 |
| 54 | TRMLTAKFAMPKKAT | 0 | 0 | 75 |

Sequence List

Useful amino acids and nucleotide sequences for practicing the invention are found in Table 7.

TABLE 7

Sequence list

| SEQ ID NUMBER | Ab region | Sequence |
|---|---|---|
| SEQ ID NO: 1 | Human IL-2 | MYRMQLLSCIALSLALVTNSAPTSSSTKKTQLQLEHL LLDLQMILNGINNYKNPKLTRMLTFKFYMPKKATELK HLQCLEEELKPLEEVLNLAQSKNFHLRPRDLISNINV IVLELKGSETTFMCEYADETATIVEFLNRWITFCQSI ISTLT |
| SEQ ID NO: 2 | Proleukin | MAPTSSSTKKTQLQLEHLLLDLQMILNGINNYKNPKL TRMLTFKFYMPKKATELKHLQCLEEELKPLEEVLNLA QSKNFHLRPRDLISNINVIVLELKGSETTFMCEYADE TATIVEFLNRWITFSQSIISILT |

Antibody 1

| SEQ ID NO: 3 | DNA Heavy Chain | ATGGAATGGAGCGGAGTCTTTATCTTTCTCCTGTCAG TAACTGCAGGTGTTCACTCCCAGGTCCAGCTGCAGCA GTCTGGAGCTGAGCTGGTAAGGCCTGGGACTTCAGTG AAGGTGTCCTGCAAGGCTTCTGGATACGCCTTCACTA ATTACTTGATAGAGTGGGTAAAGCAGAGGCCTGGACA GGGCCTTGAGTGGATTGGAGTGATTAATCCTGGAAGT GGTGGTACTAACTACAATGAGAAGTTCAAGGGCAAGG CAACACTGACTGCAGACAAATCCTCCAGCACTGCCTA CATGCAGCTCAGCAGCCTGACATCTGATGACTCTGCG GTCTATTTCTGTGCAAGATGGAGGGGGGATGGTTACT ACGCGTACTTCGATGTCTGGGGCGCAGGGACCACGGT CACCGTCTCCTCAGCCAAAACAACAGCCCCATCGGTC TATCCACTGGCCCCTGTGTGTGGAGATACAACTGGCT CCTCGGTGACTCTAGGATGCCTGGTCAAGGGTTATTT CCCTGAGCCAGTGACCTTGACCTGGAACTCTGGATCC CTGTCCAGTGGTGTGCACACCTTCCCAGCTGTCCTGC |

TABLE 7-continued

Sequence list

| SEQ ID NUMBER | Ab region | Sequence |
|---|---|---|
| | | AGTCTGACCTCTACACCCTCAGCAGCTCAGTGACTGT<br>AACCTCGAGCACCTGGCCCAGCCAGTCCATCACCTGC<br>AATGTGGCCCACCCGGCAAGCAGCACCAAGGTGGACA<br>AGAAAATTGAGCCCAGAGGGCCCACAATCAAGCCCTG<br>TCCTCCATGCAAATGCCCAGCACCTAACCTCTTGGGT<br>GGACCATCCGTCTTCATCTTCCCTCCAAAGATCAAGG<br>ATGTACTCATGATCTCCCTGAGCCCCATAGTCACATG<br>TGTGGTGGTGGATGTGAGCGAGGATGACCCAGATGTC<br>CAGATCAGCTGGTTTGTGAACAACGTGGAAGTACACA<br>CAGCTCAGACACAAACCCATAGAGAGGATTACAACAG<br>TACTCTCCGGGTGGTCAGTGCCCTCCCCATCCAGCAC<br>CAGGACTGGATGAGTGGCAAGGAGTTCAAATGCAAGG<br>TCAACAACAAAGACCTCCCAGCGCCCATCGAGAGAAC<br>CATCTCAAAACCCAAAGGGTCAGTAAGAGCTCCACAG<br>GTATATGTCTTGCCTCCACCAGAAGAAGAGATGACTA<br>AGAAACAGGTCACTCTGACCTGCATGGTCACAGACTT<br>CATGCCTGAAGACATTTACGTGGAGTGGACCAACAAC<br>GGGAAAACAGAGCTAAACTACAAGAACACTGAACCAG<br>TCCTGGACTCTGATGGTTCTTACTTCATGTACAGCAA<br>GCTGAGAGTGGAAAAGAAGAACTGGGTGGAAAGAAAT<br>AGCTACTCCTGTTCAGTGGTCCACGAGGGTCTGCACA<br>ATCACCACACGACTAAGAGCTTCTCCCGGACTCCGGG<br>TAAATGA |
| SEQ ID NO: 4 | DNA Light Chain | ATGGAGACAGACACAATCCTGCTATGGGTGCTGCTGC<br>TCTGGGTTCCAGGCTCCACTGGTGACATTGTGCTGAC<br>CCAATCTCCAGCTTCTTTGGCTGTGTCTCTAGGGCAG<br>AGGGCCACCATCTCCTGCAAGGCCAGCCAAAGTGTTG<br>ATTATGATGGTGATAGTTATATGAACTGGTACCAACA<br>GAAACCAGGACAGCCACCCAAACTCCTCATCTATGCT<br>GCATCCAATCTAGAATCTGGGATCCCAGCCAGGTTTA<br>GTGGCAGTGGGTCTGGGACAGACTTCACCCTCAACAT<br>CCATCCTGTGGAGGAGGAGGATGCTGCAACCTATTAC<br>TGTCAGCAAAGTAATGAGGATCCGTACACGTTCGGAG<br>GGGGGACCAAGCTGGAAATAAAACGGGCTGATGCTGC<br>ACCAACTGTATCCATCTTCCCACCATCCAGTGAGCAG<br>TTAACATCTGGAGGTGCCTCAGTCGTGTGCTTCTTGA<br>ACAACTTCTACCCCAAAGACATCAATGTCAAGTGGAA<br>GATTGATGGCAGTGAACGACAAAATGGCGTCCTGAAC<br>AGTTGGACTGATCAGGACAGCAAAGACAGCACCTACA<br>GCATGAGCAGCACCCTCACGTTGACCAAGGACGAGTA<br>TGAACGACATAACAGCTATACCTGTGAGGCCACTCAC<br>AAGACATCAACTTCACCCATTGTCAAGAGCTTCAACA<br>GGAATGAGTGTTAG |
| SEQ ID NO: 5 | Heavy Chain | MEWSGVFIFLLSVTAGVHSQVQLQQSGAELVRPGTSV<br>KVSCKASGYAFTNYLIEWVKQRPGQGLEWIGVINPGS<br>GGTNYNEKFKGKATLTADKSSSTAYMQLSSLTSDDSA<br>VYFCARWRGDGYYAYFDVWGAGTIVIVSSAKTTAPSV<br>YPLAPVCGDTTGSSVTLGCLVKGYFPEPVTLTWNSGS<br>LSSGVHTFPAVLQSDLYTLSSSVTVTSSTWPSQSITC<br>NVAHPASSTKVDKKIEPRGPTIKPCPPCKCPAPNLLG<br>GPSVFIFPPKIKDVLMISLSPIVTCVVVDVSEDDPDV<br>QISWFVNNVEVHTAQTQTHREDYNSTLRVVSALPIQH<br>QDWMSGKEFKCKVNNKDLPAPIERTISKPKGSVRAPQ<br>VYVLPPPEEEMTKKQVTLTCMVTDFMPEDIYVEWTNN<br>GKTELNYKNTEPVLDSDGSYFMYSKLRVEKKNWVERN<br>SYSCSVVHEGLHNHHTTKSFSRTPGK |
| SEQ ID NO: 6 | Light Chain | METDTILLWVLLLWVPGSTGDIVLTQSPASLAVSLGQ<br>RATISCKASQSVDYDGDSYMNWYQQKPGQPPKLLIYA<br>ASNLESGIPARFSGSGSGTDFTLNIHPVEEEDAATYY<br>CQQSNEDPYTFGGGTKLEIKRADAAPTVSIFPPSSEQ<br>LTSGGASVVCFLNNFYPKDINVKWKIDGSERQNGVLN<br>SWIDQDSKDSTYSMSSTLTLTKDEYERHNSYTCEATH<br>KTSTSPIVKSFNRNEC |
| SEQ ID NO: 7 (Kabat) | HCDR1 | NYLIE |
| SEQ ID NO: 8 (Kabat) | HCDR2 | VINPGSGGTNYNEKFKG |
| SEQ ID NO: 9 (Kabat) | HCDR3 | WRGDGYYAYFDV |

TABLE 7-continued

Sequence list

| SEQ ID NUMBER | Ab region | Sequence |
|---|---|---|
| SEQ ID NO: 10 (Kabat) | LCDR1 | KASQSVDYDGDSYMN |
| SEQ ID NO: 11 (Kabat) | LCDR2 | AASNLES |
| SEQ ID NO: 12 (Kabat) | LCDR3 | QQSNEDPYT |
| SEQ ID NO: 13 | HCDR1 DNA | AATTACTTGATAGAG |
| SEQ ID NO: 14 | HCDR2 DNA | GTGATTAATCCTGGAAGTGGTGGTACTAACTACAATG AGAAGTTCAAGGGC |
| SEQ ID NO: 15 | HCDR3 DNA | TGGAGGGGGGATGGTTACTACGCGTACTTCGATGTC |
| SEQ ID NO: 16 | LCDR1 DNA | AAGGCCAGCCAAAGTGTTGATTATGATGGTGATAGTT ATATGAAC |
| SEQ ID NO: 17 | LCDR2 DNA | GCTGCATCCAATCTAGAATCT |
| SEQ ID NO: 18 | LCDR3 DNA | CAGCAAAGTAATGAGGATCCGTACACG |
| SEQ ID NO: 19 | VH | QVQLQQSGAELVRPGTSVKVSCKASGYAFTNYLIEWV KQRPGQGLEWIGVINPGSGGTNYNEKFKGKATLTADK SSSTAYMQLSSLTSDDSAVYFCARWRGDGYYAYFDVW GAGTTVTVSS |
| SEQ ID NO: 20 | VL | DIVLTQSPASLAVSLGQRATISCKASQSVDYDGDSYM NWYQQKPGQPPKLLIYAASNLESGIPARFSGSGSGTD FTLNIHPVEEEDAATYYCQQSNEDPYTFGGGTKLEIK |
| SEQ ID NO: 21 | DNA VH | CAGGTCCAGCTGCAGCAGTCTGGAGCTGAGCTGGTAA GGCCTGGGACTTCAGTGAAGGTGTCCTGCAAGGCTTC TGGATACGCCTTCACTAATTACTTGATAGAGTGGGTA AAGCAGAGGCCTGGACAGGGCCTTGAGTGGATTGGAG TGATTAATCCTGGAAGTGGTGGTACTAACTACAATGA GAAGTTCAAGGGCAAGGCAACACTGACTGCAGACAAA TCCTCCAGCACTGCCTACATGCAGCTCAGCAGCCTGA CATCTGATGACTCTGCGGTCTATTTCTGTGCAAGATG GAGGGGGGATGGTTACTACGCGTACTTCGATGTCTGG GGCGCAGGGACCACGGTCACCGTCTCCTCA |
| SEQ ID NO: 22 | DNA VL | GACATTGTGCTGACCCAATCTCCAGCTTCTTTGGCTG TGTCTCTAGGGCAGAGGGCCACCATCTCCTGCAAGGC CAGCCAAAGTGTTGATTATGATGGTGATAGTTATATG AACTGGTACCAACAGAAACCAGGACAGCCACCCAAAC TCCTCATCTATGCTGCATCCAATCTAGAATCTGGGAT CCCAGCCAGGTTTAGTGGCAGTGGGTCTGGGACAGAC TTCACCCTCAACATCCATCCTGTGGAGGAGGAGGATG CTGCAACCTATTACTGTCAGCAAAGTAATGAGGATCC GTACACGTTCGGAGGGGGGACCAAGCTGGAAATAAAA |
| SEQ ID NO: 23 | Heavy chain fusion | MYRMQLLSCIALSLALVTNSAPTSSSTKKTQLQLEHL LLDLQMILNGINNYKNPKLTRMLTFKFYMPKKATELK HLQCLEEELKPLEEVLNLAQSKNFHLRPRDLISNINV IVLELKGSETTFMCEYADETATIVEFLNRWITFCQSI ISTLTGGGGSGGGGSGGGGSGGQVQLQQSGAELVRPG TSVKVSCKASGYAFTNYLIEWVKQRPGQGLEWIGVIN PGSGGTNYNEKFKGKATLTADKSSSTAYMQLSSLTSD DSAVYFCARWRGDGYYAYFDVWGAGTIVIVSSAKTTA PSVYPLAPVCGDTTGSSVTLGCLVKGYFPEPVTLTWN SGSLSSGVHTFPAVLQSDLYTLSSSVTVTSSTWPSQS ITCNVAHPASSTKVDKKIEPRGPTIKPCPPCKCPAPN LLGGPSVFIFPPKIKDVLMISLSPIVTCVVVDVSEDD PDVQISWFVNNVEVHTAQTQTHREDYNSTLRVVSALP IQHQDWMSGKEFKCKVNNKDLPAPIERTISKPKGSVR APQVYVLPPPEEEMTKKQVTLTCMVTDFMPEDIYVEW TNNGKTELNYKNTEPVLDSDGSYFMYSKLRVEKKNWV ERNSYSCSVVHEGLHNHHTTKSFSRTPGK |

TABLE 7-continued

Sequence list

| SEQ ID NUMBER | Ab region | Sequence |
| --- | --- | --- |
| SEQ ID NO: 24 | Light chain fusion | MYRMQLLSCIALSLALVTNSAPTSSSTKKTQLQLEHL LLDLQMILNGINNYKNPKLTRMLTFKFYMPKKATELK HLQCLEEELKPLEEVLNLAQSKNFHLRPRDLISNINV IVLELKGSETTFMCEYADETATIVEFLNRWITFCQSI ISTLTGGGGSGGGGSGGGGSGGDIVLTQSPASLAVSL GQRATISCKASQSVDYDGDSYMNWYQQKPGQPPKLLI YAASNLESGIPARFSGSGSGTDFTLNIHPVEEEDAAT YYCQQSNEDPYTFGGGTKLEIKRADAAPTVSIFPPSS EQLTSGGASVVCFLNNFYPKDINVKWKIDGSERQNGV LNSWTDQDSKDSTYSMSSTLTLTKDEYERHNSYTCEA THKTSTSPIVKSFNRNEC |

What is claimed is:

1. A human interleukin-2 (hIL-2) specific monoclonal antibody (mAb), or a hIL-2 specific antigen binding fragment thereof comprising a heavy chain complementarity determining region (HCDR) HCDR1 according to SEQ ID NO: 7, HCDR2 according to SEQ ID NO: 8, HCDR3 according to SEQ ID NO: 9, a light chain complementarity determining region (LCDR) LCDR1 according to SEQ ID NO: 10, LCDR2 according to SEQ ID NO: 11, LCDR3 according to SEQ ID NO: 12, wherein binding of said antibody, or antigen binding fragment thereof, to hIL-2 inhibits binding of hIL-2 to CD25.

2. The hIL-2 specific monoclonal antibody, or antigen binding fragment thereof, according to claim 1, characterized in that it comprises at least one heavy chain variable region (VH) and/or one light chain variable region (VL) sequence having a sequence identity of ≥90% compared to SEQ ID NOs 019 or 20, and wherein the hIL-2 specific monoclonal antibody, or antigen binding fragment thereof, comprises the HCDR1 according to SEQ ID NO: 7, the HCDR2 according to SEQ ID NO: 8, the HCDR3 according to SEQ ID NO: 9, the LCDR1 according to SEQ ID NO: 10, the LCDR2 according to SEQ ID NO: 11, the LCDR3 according to SEQ ID NO: 12.

3. The hIL-2 specific monoclonal antibody, or antigen binding fragment thereof, according to claim 1, wherein the antibody, or antigen binding fragment thereof, displays no measurable cross-reactivity to murine IL-2.

4. The antibody or antigen binding fragment thereof of claim 1, which binds to a hIL-2 epitope comprising the amino acids K52, P54, K55, T57, R58, T61, F62, K63, Q94, and K96 of the amino acid sequence of SEQ ID NO:1.

5. The antibody or antigen binding fragment thereof according to claim 4, wherein the epitope further comprises any one or more of the amino acids N50, N53, N91, L92, A93, N97 of the amino acid sequence of SEQ ID NO:1.

6. The hIL-2 specific monoclonal antibody, or antigen binding fragment thereof, according to claim 1, comprising at least one VH and/or at least one VL sequence, wherein said VH and/or VL sequence comprises SEQ ID NOs 019 or 20.

7. The hIL-2 specific monoclonal antibody, or antigen binding fragment thereof, according to claim 1, comprising an amino acid sequence of having a sequence identity of ≥90% to SEQ ID NOs 005 or 006, and wherein the hIL-2 specific monoclonal antibody, or antigen binding fragment thereof, comprises the HCDR1 according to SEQ ID NO: 7, the HCDR2 according to SEQ ID NO: 8, the HCDR3 according to SEQ ID NO: 9, the LCDR1 according to SEQ ID NO: 10, the LCDR2 according to SEQ ID NO: 11, the LCDR3 according to SEQ ID NO: 12.

8. The hIL-2 specific monoclonal antibody, or antigen binding fragment thereof, according to claim 1, comprising at least one amino acid sequence of SEQ ID NOs 005 or 006.

9. A therapeutic formulation comprising the hIL-2 monoclonal antibody (mAb), or the antigen binding fragment thereof, according to claim 1 and human interleukin-2 and a pharmaceutically acceptable carrier.

10. A therapeutic formulation comprising a fusion protein and a pharmaceutically acceptable carrier, wherein said fusion protein comprises:
 a. an hIL-2 binding polypeptide fragment comprising HCDR1 according to SEQ ID NO: 7, HCDR2 according to SEQ ID NO: 8, HCDR3 according to SEQ ID NO: 9, LCDR1 according to SEQ ID NO: 10, LCDR2 according to SEQ ID NO: 11, LCDR3 according to SEQ ID NO: 12, wherein the hIL-2 binding polypeptide fragment binds to hIL-2 and inhibits the binding of hIL-2 to CD25,
 b. a human IL-2 polypeptide fragment having an identity of ≥90% compared to SEQ ID NO 001, and, optionally,
 c. an amino acid linker of 1 to 50 amino acids, linking the hIL-2 binding polypeptide fragment to the human IL-2 polypeptide fragment as one single polypeptide chain.

11. The therapeutic formulation of claim 10, wherein the amino acid linker is 5 to 40 amino acids in length.

12. The therapeutic formulation of claim 10, wherein the amino acid linker is 10 to 30 amino acids in length.

13. The therapeutic formulation of claim 10, wherein the amino acid linker is 15 to 25 amino acids in length.

14. The therapeutic formulation of claim 10, wherein the hIL-2 binding polypeptide fragment is further characterized as:
 a. comprising an amino acid sequence having an identity of ≥90% compared to SEQ ID NO: 19 or SEO ID NO: 20, wherein said hIL-2 binding polypeptide fragment comprises the HCDR1 according to SEQ ID NO: 7, the HCDR2 according to SEQ ID NO: 8, the HCDR3 according to SEQ ID NO: 9, the LCDR1 according to SEQ ID NO: 10, the LCDR2 according to SEQ ID NO: 11, the LCDR3 according to SEQ ID NO: 12; and/or
 b. displaying no measurable cross reactivity to murine IL-2.

15. A nucleic acid molecule encoding the hIL-2 specific monoclonal antibody, or antigen binding fragment thereof, according to claim 1.

16. The nucleic acid molecule of claim 15, wherein said nucleic acid molecule has ≥90% sequence identity compared to SEQ ID NOs 003 or 004 and wherein said nucleic acid encodes the HCDR1 according to SEQ ID NO: 7, the HCDR2 according to SEQ ID NO: 8, the HCDR3 according to SEQ ID NO: 9, the LCDR1 according to SEQ ID NO: 10, the LCDR2 according to SEQ ID NO: 11, the LCDR3 according to SEQ ID NO: 12.

17. The nucleic acid molecule according to claim 15, wherein said nucleic acid molecule encodes the hIL-2 specific monoclonal antibody, or antigen binding fragment thereof, according to claim 2.

18. The nucleic acid molecule according to claim 15, wherein said nucleic acid molecule encodes the hIL-2 specific monoclonal antibody, or antigen binding fragment thereof, according to claim 6.

19. The nucleic acid molecule according to claim 15, wherein said nucleic acid molecule encodes the hIL-2 specific monoclonal antibody, or antigen binding fragment thereof, according to claim 7.

20. The nucleic acid molecule according to claim 15, wherein said nucleic acid molecule encodes the hIL-2 specific monoclonal antibody, or antigen binding fragment thereof, according to claim 8.

21. A vector comprising the nucleic acid molecule of claim 15.

22. A cell comprising the nucleic acid molecule according to claim 15 or expressing the nucleic acid molecule according to claim 15.

23. A cell expressing hIL-2 specific monoclonal antibody (mAb), or antigen binding fragment thereof, according to claim 1.

24. A monoclonal antibody-producing hybridoma cell line that produces the hIL-2 specific antibody, or antibody fragment thereof, of claim 1.

25. A method of treating cancer or viral infection by (1) selecting a patient having cancer or viral infection and (2) administering a therapeutically effective amount of the antibody, or antigen binding fragment thereof of claim 1, in combination with a therapeutically effective amount of human interleukin-2.

* * * * *

SEQUENCE LISTING

<160> NUMBER OF SEQ ID NOS: 84

<210> SEQ ID NO 1
<211> LENGTH: 153
<212> TYPE: PRT
<213> ORGANISM: Homo sapiens

<400> SEQUENCE: 1

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150

<210> SEQ ID NO 2
<211> LENGTH: 134
<212> TYPE: PRT
<213> ORGANISM: Homo sapiens

<400> SEQUENCE: 2

Met Ala Pro Thr Ser Ser Ser Thr Lys Lys Thr Gln Leu Gln Leu Glu
1               5                   10                  15

His Leu Leu Leu Asp Leu Gln Met Ile Leu Asn Gly Ile Asn Asn Tyr
            20                  25                  30

Lys Asn Pro Lys Leu Thr Arg Met Leu Thr Phe Lys Phe Tyr Met Pro
        35                  40                  45

```
Lys Lys Ala Thr Glu Leu Lys His Leu Gln Cys Leu Glu Glu Glu Leu
 50                  55                  60
Lys Pro Leu Glu Glu Val Leu Asn Leu Ala Gln Ser Lys Asn Phe His
 65                      70                  75                  80
Leu Arg Pro Arg Asp Leu Ile Ser Asn Ile Asn Val Ile Val Leu Glu
                     85                  90                  95
Leu Lys Gly Ser Glu Thr Thr Phe Met Cys Glu Tyr Ala Asp Glu Thr
                100                 105                 110
Ala Thr Ile Val Glu Phe Leu Asn Arg Trp Ile Thr Phe Ser Gln Ser
            115                 120                 125
Ile Ile Ser Thr Leu Thr
            130

<210> SEQ ID NO 3
<211> LENGTH: 1413
<212> TYPE: DNA
<213> ORGANISM: Mus musculus

<400> SEQUENCE: 3
atggaatgga gcggagtctt tatctttctc ctgtcagtaa ctgcaggtgt tcactcccag     60
gtccagctgc agcagtctgg agctgagctg gtaaggcctg gacttcagt gaaggtgtcc    120 tgcaaggctt ctggatacgc cttcactaat tacttgatag agtgggtaaa gcagaggcct    180
ggacagggcc ttgagtggat tggagtgatt aatcctggaa gtggtggtac taactacaat    240
gagaagttca gggcaaggc aacactgact gcagacaaat cctccagcac tgcctacatg    300
cagctcagca gcctgacatc tgatgactct gcggtctatt tctgtgcaag atggaggggg    360
gatggttact acgcgtactt cgatgtctgg ggcgcaggga ccacggtcac cgtctcctca    420
gccaaaacaa cagccccatc ggtctatcca ctggcccctg tgtgtggaga tacaactggc    480
tcctcggtga ctctaggatg cctggtcaag ggttatttcc ctgagccagt gaccttgacc    540
tggaactctg gatccctgtc cagtggtgtg cacaccttcc cagctgtcct gcagtctgac    600
ctctacaccc tcagcagctc agtgactgta acctcgagca cctggcccag ccagtccatc    660
acctgcaatg tggcccaccc ggcaagcagc accaaggtgg acaagaaaat tgagcccaga    720
gggcccacaa tcaagccctg tcctccatgc aaatgcccag cacctaacct cttgggtgga    780
ccatccgtct tcatcttccc tccaaagatc aaggatgtac tcatgatctc cctgagcccc    840
atagtcacat gtgtggtggt ggatgtgagc gaggatgacc cagatgtcca gatcagctgg    900
tttgtgaaca acgtggaagt acacacagct cagacacaaa cccatagaga ggattacaac    960
agtactctcc gggtggtcag tgccctcccc atccagcacc aggactggat gagtggcaag   1020
gagttcaaat gcaaggtcaa caacaaagac ctcccagcgc catcgagag aaccatctca   1080 aaacccaaag ggtcagtaag agctccacag gtatatgtct tgcctccacc agaagaagag   1140
atgactaaga aacaggtcac tctgacctgc atggtcacag acttcatgcc tgaagacatt   1200
tacgtggagt ggaccaacaa cgggaaaaca gagctaaact acaagaacac tgaaccagtc   1260
ctggactctg atggttctta cttcatgtac agcaagctga gagtggaaaa gaagaactgg   1320
gtggaaagaa atagctactc ctgttcagtg gtccacgagg tctgcacaa tcaccacacg   1380 actaagagct tctcccggac tccgggtaaa tga                                1413

<210> SEQ ID NO 4
<211> LENGTH: 717
<212> TYPE: DNA
```

<213> ORGANISM: Mus musculus

<400> SEQUENCE: 4

```
atggagacag acacaatcct gctatgggtg ctgctgctct gggttccagg ctccactggt    60
gacattgtgc tgacccaatc tccagcttct ttggctgtgt ctctagggca gagggccacc   120
atctcctgca aggccagcca aagtgttgat tatgatggtg atagttatat gaactggtac   180
caacagaaac caggacagcc acccaaactc ctcatctatg ctgcatccaa tctagaatct   240
gggatcccag ccaggtttag tggcagtggg tctgggacag acttcaccct caacatccat   300
cctgtggagg aggaggatgc tgcaacctat tactgtcagc aaagtaatga ggatccgtac   360
acgttcggag gggggaccaa gctggaaata aaacggctga tgctgcacc aactgtatcc   420
atcttcccac catccagtga gcagttaaca tctggaggtg cctcagtcgt gtgcttcttg   480
aacaacttct accccaaaga catcaatgtc aagtggaaga ttgatggcag tgaacgacaa   540
aatggcgtcc tgaacagttg gactgatcag gacagcaaag acagcaccta cagcatgagc   600
agcaccctca cgttgaccaa ggacgagtat gaacgacata cagctatac ctgtgaggcc    660
actcacaaga catcaacttc acccattgtc aagagcttca caggaatga gtgttag      717
```

<210> SEQ ID NO 5
<211> LENGTH: 470
<212> TYPE: PRT
<213> ORGANISM: Mus musculus

<400> SEQUENCE: 5

```
Met Glu Trp Ser Gly Val Phe Ile Phe Leu Leu Ser Val Thr Ala Gly
  1               5                  10                  15

Val His Ser Gln Val Gln Leu Gln Gln Ser Gly Ala Glu Leu Val Arg
             20                  25                  30

Pro Gly Thr Ser Val Lys Val Ser Cys Lys Ala Ser Gly Tyr Ala Phe
         35                  40                  45

Thr Asn Tyr Leu Ile Glu Trp Val Lys Gln Arg Pro Gly Gln Gly Leu
     50                  55                  60

Glu Trp Ile Gly Val Ile Asn Pro Gly Ser Gly Gly Thr Asn Tyr Asn
 65                  70                  75                  80

Glu Lys Phe Lys Gly Lys Ala Thr Leu Thr Ala Asp Lys Ser Ser Ser
                 85                  90                  95

Thr Ala Tyr Met Gln Leu Ser Ser Leu Thr Ser Asp Asp Ser Ala Val
            100                 105                 110

Tyr Phe Cys Ala Arg Trp Arg Gly Asp Gly Tyr Tyr Ala Tyr Phe Asp
        115                 120                 125

Val Trp Gly Ala Gly Thr Thr Val Thr Val Ser Ser Ala Lys Thr Thr
    130                 135                 140

Ala Pro Ser Val Tyr Pro Leu Ala Pro Val Cys Gly Asp Thr Thr Gly
145                 150                 155                 160

Ser Ser Val Thr Leu Gly Cys Leu Val Lys Gly Tyr Phe Pro Glu Pro
                165                 170                 175

Val Thr Leu Thr Trp Asn Ser Gly Ser Leu Ser Ser Gly Val His Thr
            180                 185                 190

Phe Pro Ala Val Leu Gln Ser Asp Leu Tyr Thr Leu Ser Ser Ser Val
        195                 200                 205

Thr Val Thr Ser Ser Thr Trp Pro Ser Gln Ser Ile Thr Cys Asn Val
    210                 215                 220

Ala His Pro Ala Ser Ser Thr Lys Val Asp Lys Lys Ile Glu Pro Arg
```

```
            225                 230                 235                 240
Gly Pro Thr Ile Lys Pro Cys Pro Cys Lys Cys Pro Ala Pro Asn
                245                 250                 255

Leu Leu Gly Gly Pro Ser Val Phe Ile Phe Pro Pro Lys Ile Lys Asp
                260                 265                 270

Val Leu Met Ile Ser Leu Ser Pro Ile Val Thr Cys Val Val Val Asp
                275                 280                 285

Val Ser Glu Asp Asp Pro Asp Val Gln Ile Ser Trp Phe Val Asn Asn
            290                 295                 300

Val Glu Val His Thr Ala Gln Thr Gln Thr His Arg Glu Asp Tyr Asn
305                 310                 315                 320

Ser Thr Leu Arg Val Val Ser Ala Leu Pro Ile Gln His Gln Asp Trp
                325                 330                 335

Met Ser Gly Lys Glu Phe Lys Cys Lys Val Asn Asn Lys Asp Leu Pro
                340                 345                 350

Ala Pro Ile Glu Arg Thr Ile Ser Lys Pro Lys Gly Ser Val Arg Ala
                355                 360                 365

Pro Gln Val Tyr Val Leu Pro Pro Pro Glu Glu Glu Met Thr Lys Lys
            370                 375                 380

Gln Val Thr Leu Thr Cys Met Val Thr Asp Phe Met Pro Glu Asp Ile
385                 390                 395                 400

Tyr Val Glu Trp Thr Asn Asn Gly Lys Thr Glu Leu Asn Tyr Lys Asn
                405                 410                 415

Thr Glu Pro Val Leu Asp Ser Asp Gly Ser Tyr Phe Met Tyr Ser Lys
                420                 425                 430

Leu Arg Val Glu Lys Lys Asn Trp Val Glu Arg Asn Ser Tyr Ser Cys
            435                 440                 445

Ser Val Val His Glu Gly Leu His Asn His His Thr Thr Lys Ser Phe
                450                 455                 460

Ser Arg Thr Pro Gly Lys
465                 470

<210> SEQ ID NO 6
<211> LENGTH: 238
<212> TYPE: PRT
<213> ORGANISM: Mus musculus

<400> SEQUENCE: 6

Met Glu Thr Asp Thr Ile Leu Leu Trp Val Leu Leu Trp Val Pro
1               5                   10                  15

Gly Ser Thr Gly Asp Ile Val Leu Thr Gln Ser Pro Ala Ser Leu Ala
                20                  25                  30

Val Ser Leu Gly Gln Arg Ala Thr Ile Ser Cys Lys Ala Ser Gln Ser
            35                  40                  45

Val Asp Tyr Asp Gly Asp Ser Tyr Met Asn Trp Tyr Gln Gln Lys Pro
        50                  55                  60

Gly Gln Pro Pro Lys Leu Leu Ile Tyr Ala Ala Ser Asn Leu Glu Ser
65                  70                  75                  80

Gly Ile Pro Ala Arg Phe Ser Gly Ser Gly Ser Gly Thr Asp Phe Thr
                85                  90                  95

Leu Asn Ile His Pro Val Glu Glu Asp Ala Ala Thr Tyr Tyr Cys
                100                 105                 110

Gln Gln Ser Asn Glu Asp Pro Tyr Thr Phe Gly Gly Gly Thr Lys Leu
            115                 120                 125
```

```
Glu Ile Lys Arg Ala Asp Ala Ala Pro Thr Val Ser Ile Phe Pro Pro
130                 135                 140
Ser Ser Glu Gln Leu Thr Ser Gly Gly Ala Ser Val Val Cys Phe Leu
145                 150                 155                 160
Asn Asn Phe Tyr Pro Lys Asp Ile Asn Val Lys Trp Lys Ile Asp Gly
                165                 170                 175
Ser Glu Arg Gln Asn Gly Val Leu Asn Ser Trp Thr Asp Gln Asp Ser
            180                 185                 190
Lys Asp Ser Thr Tyr Ser Met Ser Ser Thr Leu Thr Leu Thr Lys Asp
        195                 200                 205
Glu Tyr Glu Arg His Asn Ser Tyr Thr Cys Glu Ala Thr His Lys Thr
210                 215                 220
Ser Thr Ser Pro Ile Val Lys Ser Phe Asn Arg Asn Glu Cys
225                 230                 235
```

<210> SEQ ID NO 7
<211> LENGTH: 5
<212> TYPE: PRT
<213> ORGANISM: Mus musculus

<400> SEQUENCE: 7

```
Asn Tyr Leu Ile Glu
1               5
```

<210> SEQ ID NO 8
<211> LENGTH: 17
<212> TYPE: PRT
<213> ORGANISM: Mus musculus

<400> SEQUENCE: 8

```
Val Ile Asn Pro Gly Ser Gly Gly Thr Asn Tyr Asn Glu Lys Phe Lys
1               5                   10                  15
Gly
```

<210> SEQ ID NO 9
<211> LENGTH: 12
<212> TYPE: PRT
<213> ORGANISM: Mus musculus

<400> SEQUENCE: 9

```
Trp Arg Gly Asp Gly Tyr Tyr Ala Tyr Phe Asp Val
1               5                   10
```

<210> SEQ ID NO 10
<211> LENGTH: 15
<212> TYPE: PRT
<213> ORGANISM: Mus musculus

<400> SEQUENCE: 10

```
Lys Ala Ser Gln Ser Val Asp Tyr Asp Gly Asp Ser Tyr Met Asn
1               5                   10                  15
```

<210> SEQ ID NO 11
<211> LENGTH: 7
<212> TYPE: PRT
<213> ORGANISM: Mus musculus

<400> SEQUENCE: 11

```
Ala Ala Ser Asn Leu Glu Ser
1               5
```

```
<210> SEQ ID NO 12
<211> LENGTH: 9
<212> TYPE: PRT
<213> ORGANISM: Mus musculus

<400> SEQUENCE: 12

Gln Gln Ser Asn Glu Asp Pro Tyr Thr
1               5

<210> SEQ ID NO 13
<211> LENGTH: 15
<212> TYPE: DNA
<213> ORGANISM: Mus musculus

<400> SEQUENCE: 13
aattacttga tagag                                                15

<210> SEQ ID NO 14
<211> LENGTH: 51
<212> TYPE: DNA
<213> ORGANISM: Mus musculus

<400> SEQUENCE: 14
gtgattaatc ctggaagtgg tggtactaac tacaatgaga agttcaaggg c         51

<210> SEQ ID NO 15
<211> LENGTH: 36
<212> TYPE: DNA
<213> ORGANISM: Mus musculus

<400> SEQUENCE: 15
tggagggggg atggttacta cgcgtacttc gatgtc                         36

<210> SEQ ID NO 16
<211> LENGTH: 45
<212> TYPE: DNA
<213> ORGANISM: Mus musculus

<400> SEQUENCE: 16
aaggccagcc aaagtgttga ttatgatggt gatagttata tgaac               45

<210> SEQ ID NO 17
<211> LENGTH: 21
<212> TYPE: DNA
<213> ORGANISM: Mus musculus

<400> SEQUENCE: 17
gctgcatcca atctagaatc t                                         21

<210> SEQ ID NO 18
<211> LENGTH: 27
<212> TYPE: DNA
<213> ORGANISM: Mus musculus

<400> SEQUENCE: 18
cagcaaagta atgaggatcc gtacacg                                   27

<210> SEQ ID NO 19
<211> LENGTH: 121
<212> TYPE: PRT
<213> ORGANISM: Mus musculus

<400> SEQUENCE: 19

Gln Val Gln Leu Gln Gln Ser Gly Ala Glu Leu Val Arg Pro Gly Thr
```

```
              1               5                  10                 15
              Ser Val Lys Val Ser Cys Lys Ala Ser Gly Tyr Ala Phe Thr Asn Tyr
                         20                  25                 30

Leu Ile Glu Trp Val Lys Gln Arg Pro Gly Gln Gly Leu Glu Trp Ile
                         35                  40                 45

Gly Val Ile Asn Pro Gly Ser Gly Gly Thr Asn Tyr Asn Glu Lys Phe
                         50                  55                 60

Lys Gly Lys Ala Thr Leu Thr Ala Asp Lys Ser Ser Thr Ala Tyr
              65                  70                  75                 80

Met Gln Leu Ser Ser Leu Thr Ser Asp Asp Ser Ala Val Tyr Phe Cys
                                   85                  90                  95

Ala Arg Trp Arg Gly Asp Gly Tyr Tyr Ala Tyr Phe Asp Val Trp Gly
                         100                 105                110

Ala Gly Thr Thr Val Thr Val Ser Ser
                         115                 120

<210> SEQ ID NO 20
<211> LENGTH: 111
<212> TYPE: PRT
<213> ORGANISM: Mus musculus

<400> SEQUENCE: 20

Asp Ile Val Leu Thr Gln Ser Pro Ala Ser Leu Ala Val Ser Leu Gly
              1               5                  10                 15

Gln Arg Ala Thr Ile Ser Cys Lys Ala Ser Gln Ser Val Asp Tyr Asp
                         20                  25                 30

Gly Asp Ser Tyr Met Asn Trp Tyr Gln Gln Lys Pro Gly Gln Pro Pro
                         35                  40                 45

Lys Leu Leu Ile Tyr Ala Ala Ser Asn Leu Glu Ser Gly Ile Pro Ala
                         50                  55                 60

Arg Phe Ser Gly Ser Gly Ser Gly Thr Asp Phe Thr Leu Asn Ile His
              65                  70                  75                 80

Pro Val Glu Glu Glu Asp Ala Ala Thr Tyr Tyr Cys Gln Gln Ser Asn
                                   85                  90                  95

Glu Asp Pro Tyr Thr Phe Gly Gly Gly Thr Lys Leu Glu Ile Lys
                         100                 105                110

<210> SEQ ID NO 21
<211> LENGTH: 363
<212> TYPE: DNA
<213> ORGANISM: Mus musculus

<400> SEQUENCE: 21
caggtccagc tgcagcagtc tggagctgag ctggtaaggc ctgggacttc agtgaaggtg         60
tcctgcaagg cttctggata cgccttcact aattacttga tagagtgggt aaagcagagg        120
cctggacagg gccttgagtg gattggagtg attaatcctg gaagtggtgg tactaactac        180
aatgagaagt tcaagggcaa ggcaacactg actgcagaca atcctccag cactgcctac         240 atgcagctca gcagcctgac atctgatgac tctgcggtct atttctgtgc aagatggagg        300
ggggatggtt actacgcgta cttcgatgtc tggggcgcag ggaccacggt caccgtctcc        360
tca                                                                     363

<210> SEQ ID NO 22
<211> LENGTH: 333
<212> TYPE: DNA
<213> ORGANISM: Mus musculus
```

-continued

<400> SEQUENCE: 22

| gacattgtgc | tgacccaatc | tccagcttct | ttggctgtgt | ctctagggca | gagggccacc | 60 |
| atctcctgca | aggccagcca | aagtgttgat | tatgatggtg | atagttatat | gaactggtac | 120 |
| caacagaaac | caggacagcc | acccaaactc | ctcatctatg | ctgcatccaa | tctagaatct | 180 |
| gggatcccag | ccaggtttag | tggcagtggg | tctgggacag | acttcaccct | caacatccat | 240 |
| cctgtggagg | aggaggatgc | tgcaacctat | tactgtcagc | aaagtaatga | ggatccgtac | 300 |
| acgttcggag | gggggaccaa | gctggaaata | aaa | | | 333 |

<210> SEQ ID NO 23
<211> LENGTH: 621
<212> TYPE: PRT
<213> ORGANISM: Mus musculus

<400> SEQUENCE: 23

```
Met Tyr Arg Met Gln Leu Leu Ser Cys Ile Ala Leu Ser Leu Ala Leu
1               5                   10                  15

Val Thr Asn Ser Ala Pro Thr Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr Gly Gly Gly Gly Ser Gly Gly
145                 150                 155                 160

Gly Gly Ser Gly Gly Gly Gly Ser Gly Gly Gln Val Gln Leu Gln Gln
                165                 170                 175

Ser Gly Ala Glu Leu Val Arg Pro Gly Thr Ser Val Lys Val Ser Cys
            180                 185                 190

Lys Ala Ser Gly Tyr Ala Phe Thr Asn Tyr Leu Ile Glu Trp Val Lys
        195                 200                 205

Gln Arg Pro Gly Gln Gly Leu Glu Trp Ile Gly Val Ile Asn Pro Gly
    210                 215                 220

Ser Gly Gly Thr Asn Tyr Asn Glu Lys Phe Lys Gly Lys Ala Thr Leu
225                 230                 235                 240

Thr Ala Asp Lys Ser Ser Ser Thr Ala Tyr Met Gln Leu Ser Ser Leu
                245                 250                 255

Thr Ser Asp Asp Ser Ala Val Tyr Phe Cys Ala Arg Trp Arg Gly Asp
            260                 265                 270

Gly Tyr Tyr Ala Tyr Phe Asp Val Trp Gly Ala Gly Thr Thr Val Thr
        275                 280                 285

Val Ser Ser Ala Lys Thr Thr Ala Pro Ser Val Tyr Pro Leu Ala Pro
    290                 295                 300
```

Val Cys Gly Asp Thr Thr Gly Ser Ser Val Thr Leu Gly Cys Leu Val
305                 310                 315                 320

Lys Gly Tyr Phe Pro Glu Pro Val Thr Leu Thr Trp Asn Ser Gly Ser
            325                 330                 335

Leu Ser Ser Gly Val His Thr Phe Pro Ala Val Leu Gln Ser Asp Leu
                340                 345                 350

Tyr Thr Leu Ser Ser Ser Val Thr Val Thr Ser Ser Thr Trp Pro Ser
            355                 360                 365

Gln Ser Ile Thr Cys Asn Val Ala His Pro Ala Ser Ser Thr Lys Val
370                 375                 380

Asp Lys Lys Ile Glu Pro Arg Gly Pro Thr Ile Lys Pro Cys Pro Pro
385                 390                 395                 400

Cys Lys Cys Pro Ala Pro Asn Leu Leu Gly Gly Pro Ser Val Phe Ile
                405                 410                 415

Phe Pro Pro Lys Ile Lys Asp Val Leu Met Ile Ser Leu Ser Pro Ile
            420                 425                 430

Val Thr Cys Val Val Val Asp Val Ser Glu Asp Asp Pro Asp Val Gln
        435                 440                 445

Ile Ser Trp Phe Val Asn Asn Val Glu Val His Thr Ala Gln Thr Gln
450                 455                 460

Thr His Arg Glu Asp Tyr Asn Ser Thr Leu Arg Val Val Ser Ala Leu
465                 470                 475                 480

Pro Ile Gln His Gln Asp Trp Met Ser Gly Lys Glu Phe Lys Cys Lys
            485                 490                 495

Val Asn Asn Lys Asp Leu Pro Ala Pro Ile Glu Arg Thr Ile Ser Lys
                500                 505                 510

Pro Lys Gly Ser Val Arg Ala Pro Gln Val Tyr Val Leu Pro Pro Pro
            515                 520                 525

Glu Glu Glu Met Thr Lys Lys Gln Val Thr Leu Thr Cys Met Val Thr
530                 535                 540

Asp Phe Met Pro Glu Asp Ile Tyr Val Glu Trp Thr Asn Asn Gly Lys
545                 550                 555                 560

Thr Glu Leu Asn Tyr Lys Asn Thr Glu Pro Val Leu Asp Ser Asp Gly
                565                 570                 575

Ser Tyr Phe Met Tyr Ser Lys Leu Arg Val Glu Lys Lys Asn Trp Val
            580                 585                 590

Glu Arg Asn Ser Tyr Ser Cys Ser Val Val His Glu Gly Leu His Asn
                595                 600                 605

His His Thr Thr Lys Ser Phe Ser Arg Thr Pro Gly Lys
610                 615                 620

<210> SEQ ID NO 24
<211> LENGTH: 388
<212> TYPE: PRT
<213> ORGANISM: Mus musculus

<400> SEQUENCE: 24

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
                20                  25                  30

Gln Leu Glu His Leu Leu Leu Asp Leu Gln Met Ile Leu Asn Gly Ile
            35                  40                  45

Asn Asn Tyr Lys Asn Pro Lys Leu Thr Arg Met Leu Thr Phe Lys Phe

```
            50                  55                  60
Tyr Met Pro Lys Lys Ala Thr Glu Leu Lys His Leu Gln Cys Leu Glu
 65                  70                  75                  80

Glu Glu Leu Lys Pro Leu Glu Glu Val Leu Asn Leu Ala Gln Ser Lys
                 85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr Gly Gly Gly Gly Ser Gly Gly
145                 150                 155                 160

Gly Gly Ser Gly Gly Gly Gly Ser Gly Gly Asp Ile Val Leu Thr Gln
                165                 170                 175

Ser Pro Ala Ser Leu Ala Val Ser Leu Gly Gln Arg Ala Thr Ile Ser
            180                 185                 190

Cys Lys Ala Ser Gln Ser Val Asp Tyr Asp Gly Asp Ser Tyr Met Asn
        195                 200                 205

Trp Tyr Gln Gln Lys Pro Gly Gln Pro Pro Lys Leu Leu Ile Tyr Ala
    210                 215                 220

Ala Ser Asn Leu Glu Ser Gly Ile Pro Ala Arg Phe Ser Gly Ser Gly
225                 230                 235                 240

Ser Gly Thr Asp Phe Thr Leu Asn Ile His Pro Val Glu Glu Glu Asp
                245                 250                 255

Ala Ala Thr Tyr Tyr Cys Gln Gln Ser Asn Glu Asp Pro Tyr Thr Phe
            260                 265                 270

Gly Gly Gly Thr Lys Leu Glu Ile Lys Arg Ala Asp Ala Ala Pro Thr
        275                 280                 285

Val Ser Ile Phe Pro Pro Ser Ser Glu Gln Leu Thr Ser Gly Gly Ala
    290                 295                 300

Ser Val Val Cys Phe Leu Asn Asn Phe Tyr Pro Lys Asp Ile Asn Val
305                 310                 315                 320

Lys Trp Lys Ile Asp Gly Ser Glu Arg Gln Asn Gly Val Leu Asn Ser
                325                 330                 335

Trp Thr Asp Gln Asp Ser Lys Asp Ser Thr Tyr Ser Met Ser Ser Thr
            340                 345                 350

Leu Thr Leu Thr Lys Asp Glu Tyr Glu Arg His Asn Ser Tyr Thr Cys
        355                 360                 365

Glu Ala Thr His Lys Thr Ser Thr Ser Pro Ile Val Lys Ser Phe Asn
    370                 375                 380

Arg Asn Glu Cys
385

<210> SEQ ID NO 25
<211> LENGTH: 15
<212> TYPE: PRT
<213> ORGANISM: Artificial
<220> FEATURE:
<223> OTHER INFORMATION: Ref pep no. 1

<400> SEQUENCE: 25

Ala Pro Thr Ser Ser Thr Lys Lys Thr Gln Leu Gln Leu Glu
 1               5                  10                  15
```

```
<210> SEQ ID NO 26
<211> LENGTH: 15
<212> TYPE: PRT
<213> ORGANISM: Artificial
<220> FEATURE:
<223> OTHER INFORMATION: Ref pep no. 2

<400> SEQUENCE: 26

Ser Ser Ser Thr Lys Lys Thr Gln Leu Gln Leu Glu His Leu Leu
1               5                   10                  15

<210> SEQ ID NO 27
<211> LENGTH: 15
<212> TYPE: PRT
<213> ORGANISM: Artificial
<220> FEATURE:
<223> OTHER INFORMATION: Ref pep no. 3

<400> SEQUENCE: 27

Thr Lys Lys Thr Gln Leu Gln Leu Glu His Leu Leu Leu Asp Leu
1               5                   10                  15

<210> SEQ ID NO 28
<211> LENGTH: 15
<212> TYPE: PRT
<213> ORGANISM: Artificial
<220> FEATURE:
<223> OTHER INFORMATION: Ref pep no. 4

<400> SEQUENCE: 28

Thr Gln Leu Gln Leu Glu His Leu Leu Leu Asp Leu Gln Met Ile
1               5                   10                  15

<210> SEQ ID NO 29
<211> LENGTH: 15
<212> TYPE: PRT
<213> ORGANISM: Artificial
<220> FEATURE:
<223> OTHER INFORMATION: Ref pep no. 5

<400> SEQUENCE: 29

Gln Leu Glu His Leu Leu Leu Asp Leu Gln Met Ile Leu Asn Gly
1               5                   10                  15

<210> SEQ ID NO 30
<211> LENGTH: 15
<212> TYPE: PRT
<213> ORGANISM: Artificial
<220> FEATURE:
<223> OTHER INFORMATION: Ref pep no. 6

<400> SEQUENCE: 30

His Leu Leu Leu Asp Leu Gln Met Ile Leu Asn Gly Ile Asn Asn
1               5                   10                  15

<210> SEQ ID NO 31
<211> LENGTH: 15
<212> TYPE: PRT
<213> ORGANISM: Artificial
<220> FEATURE:
<223> OTHER INFORMATION: Ref pep no. 7

<400> SEQUENCE: 31

Leu Asp Leu Gln Met Ile Leu Asn Gly Ile Asn Asn Tyr Lys Asn
1               5                   10                  15

<210> SEQ ID NO 32
```

```
<211> LENGTH: 15
<212> TYPE: PRT
<213> ORGANISM: Artificial
<220> FEATURE:
<223> OTHER INFORMATION: Ref pep no. 8

<400> SEQUENCE: 32

Gln Met Ile Leu Asn Gly Ile Asn Asn Tyr Lys Asn Pro Lys Leu
1               5                   10                  15

<210> SEQ ID NO 33
<211> LENGTH: 15
<212> TYPE: PRT
<213> ORGANISM: Artificial
<220> FEATURE:
<223> OTHER INFORMATION: Ref pep no. 9

<400> SEQUENCE: 33

Leu Asn Gly Ile Asn Asn Tyr Lys Asn Pro Lys Leu Thr Arg Met
1               5                   10                  15

<210> SEQ ID NO 34
<211> LENGTH: 15
<212> TYPE: PRT
<213> ORGANISM: Artificial
<220> FEATURE:
<223> OTHER INFORMATION: Ref pep no. 10

<400> SEQUENCE: 34

Ile Asn Asn Tyr Lys Asn Pro Lys Leu Thr Arg Met Leu Thr Phe
1               5                   10                  15

<210> SEQ ID NO 35
<211> LENGTH: 15
<212> TYPE: PRT
<213> ORGANISM: Artificial
<220> FEATURE:
<223> OTHER INFORMATION: Ref pep no. 11

<400> SEQUENCE: 35

Tyr Lys Asn Pro Lys Leu Thr Arg Met Leu Thr Phe Lys Phe Tyr
1               5                   10                  15

<210> SEQ ID NO 36
<211> LENGTH: 15
<212> TYPE: PRT
<213> ORGANISM: Artificial
<220> FEATURE:
<223> OTHER INFORMATION: Ref pep no. 12

<400> SEQUENCE: 36

Pro Lys Leu Thr Arg Met Leu Thr Phe Lys Phe Tyr Met Pro Lys
1               5                   10                  15

<210> SEQ ID NO 37
<211> LENGTH: 15
<212> TYPE: PRT
<213> ORGANISM: Artificial
<220> FEATURE:
<223> OTHER INFORMATION: Ref pep no. 13

<400> SEQUENCE: 37

Thr Arg Met Leu Thr Phe Lys Phe Tyr Met Pro Lys Lys Ala Thr
1               5                   10                  15

<210> SEQ ID NO 38
<211> LENGTH: 15
```

```
<212> TYPE: PRT
<213> ORGANISM: Artificial
<220> FEATURE:
<223> OTHER INFORMATION: Ref pep no. 14

<400> SEQUENCE: 38

Leu Thr Phe Lys Phe Tyr Met Pro Lys Lys Ala Thr Glu Leu Lys
1               5                   10                  15

<210> SEQ ID NO 39
<211> LENGTH: 15
<212> TYPE: PRT
<213> ORGANISM: Artificial
<220> FEATURE:
<223> OTHER INFORMATION: Ref pep no. 15

<400> SEQUENCE: 39

Lys Phe Tyr Met Pro Lys Lys Ala Thr Glu Leu Lys His Leu Gln
1               5                   10                  15

<210> SEQ ID NO 40
<211> LENGTH: 15
<212> TYPE: PRT
<213> ORGANISM: Artificial
<220> FEATURE:
<223> OTHER INFORMATION: Ref pep no. 16

<400> SEQUENCE: 40

Met Pro Lys Lys Ala Thr Glu Leu Lys His Leu Gln Ser Leu Glu
1               5                   10                  15

<210> SEQ ID NO 41
<211> LENGTH: 15
<212> TYPE: PRT
<213> ORGANISM: Artificial
<220> FEATURE:
<223> OTHER INFORMATION: Ref pep no. 17

<400> SEQUENCE: 41

Lys Ala Thr Glu Leu Lys His Leu Gln Ser Leu Glu Glu Glu Leu
1               5                   10                  15

<210> SEQ ID NO 42
<211> LENGTH: 15
<212> TYPE: PRT
<213> ORGANISM: Artificial
<220> FEATURE:
<223> OTHER INFORMATION: Ref pep no. 18

<400> SEQUENCE: 42

Glu Leu Lys His Leu Gln Ser Leu Glu Glu Glu Leu Lys Pro Leu
1               5                   10                  15

<210> SEQ ID NO 43
<211> LENGTH: 15
<212> TYPE: PRT
<213> ORGANISM: Artificial
<220> FEATURE:
<223> OTHER INFORMATION: Ref pep no. 19

<400> SEQUENCE: 43

His Leu Gln Ser Leu Glu Glu Glu Leu Lys Pro Leu Glu Glu Val
1               5                   10                  15

<210> SEQ ID NO 44
<211> LENGTH: 15
<212> TYPE: PRT
```

<213> ORGANISM: Artificial
<220> FEATURE:
<223> OTHER INFORMATION: Ref pep no. 20

<400> SEQUENCE: 44

Ser Leu Glu Glu Glu Leu Lys Pro Leu Glu Glu Val Leu Asn Leu
1               5                   10                  15

<210> SEQ ID NO 45
<211> LENGTH: 15
<212> TYPE: PRT
<213> ORGANISM: Artificial
<220> FEATURE:
<223> OTHER INFORMATION: Ref pep no. 21

<400> SEQUENCE: 45

Glu Glu Leu Lys Pro Leu Glu Glu Val Leu Asn Leu Ala Gln Ser
1               5                   10                  15

<210> SEQ ID NO 46
<211> LENGTH: 15
<212> TYPE: PRT
<213> ORGANISM: Artificial
<220> FEATURE:
<223> OTHER INFORMATION: Ref pep no. 22

<400> SEQUENCE: 46

Lys Pro Leu Glu Glu Val Leu Asn Leu Ala Gln Ser Lys Asn Phe
1               5                   10                  15

<210> SEQ ID NO 47
<211> LENGTH: 15
<212> TYPE: PRT
<213> ORGANISM: Artificial
<220> FEATURE:
<223> OTHER INFORMATION: Ref pep no. 23

<400> SEQUENCE: 47

Glu Glu Val Leu Asn Leu Ala Gln Ser Lys Asn Phe His Leu Arg
1               5                   10                  15

<210> SEQ ID NO 48
<211> LENGTH: 15
<212> TYPE: PRT
<213> ORGANISM: Artificial
<220> FEATURE:
<223> OTHER INFORMATION: Ref pep no. 24

<400> SEQUENCE: 48

Leu Asn Leu Ala Gln Ser Lys Asn Phe His Leu Arg Pro Arg Asp
1               5                   10                  15

<210> SEQ ID NO 49
<211> LENGTH: 15
<212> TYPE: PRT
<213> ORGANISM: Artificial
<220> FEATURE:
<223> OTHER INFORMATION: Ref pep no. 25

<400> SEQUENCE: 49

Ala Gln Ser Lys Asn Phe His Leu Arg Pro Arg Asp Leu Ile Ser
1               5                   10                  15

<210> SEQ ID NO 50
<211> LENGTH: 15
<212> TYPE: PRT
<213> ORGANISM: Artificial

<220> FEATURE:
<223> OTHER INFORMATION: Ref pep no. 26

<400> SEQUENCE: 50

```
Lys Asn Phe His Leu Arg Pro Arg Asp Leu Ile Ser Asn Ile Asn
1               5                   10                  15
```

<210> SEQ ID NO 51
<211> LENGTH: 15
<212> TYPE: PRT
<213> ORGANISM: Artificial
<220> FEATURE:
<223> OTHER INFORMATION: Ref pep no. 27

<400> SEQUENCE: 51

```
His Leu Arg Pro Arg Asp Leu Ile Ser Asn Ile Asn Val Ile Val
1               5                   10                  15
```

<210> SEQ ID NO 52
<211> LENGTH: 15
<212> TYPE: PRT
<213> ORGANISM: Artificial
<220> FEATURE:
<223> OTHER INFORMATION: Ref pep no. 28

<400> SEQUENCE: 52

```
Pro Arg Asp Leu Ile Ser Asn Ile Asn Val Ile Val Leu Glu Leu
1               5                   10                  15
```

<210> SEQ ID NO 53
<211> LENGTH: 15
<212> TYPE: PRT
<213> ORGANISM: Artificial
<220> FEATURE:
<223> OTHER INFORMATION: Ref pep no. 29

<400> SEQUENCE: 53

```
Leu Ile Ser Asn Ile Asn Val Ile Val Leu Glu Leu Lys Gly Ser
1               5                   10                  15
```

<210> SEQ ID NO 54
<211> LENGTH: 15
<212> TYPE: PRT
<213> ORGANISM: Artificial
<220> FEATURE:
<223> OTHER INFORMATION: Ref pep no. 30

<400> SEQUENCE: 54

```
Asn Ile Asn Val Ile Val Leu Glu Leu Lys Gly Ser Glu Thr Thr
1               5                   10                  15
```

<210> SEQ ID NO 55
<211> LENGTH: 15
<212> TYPE: PRT
<213> ORGANISM: Artificial
<220> FEATURE:
<223> OTHER INFORMATION: Ref pep no. 31

<400> SEQUENCE: 55

```
Val Ile Val Leu Glu Leu Lys Gly Ser Glu Thr Thr Phe Met Ser
1               5                   10                  15
```

<210> SEQ ID NO 56
<211> LENGTH: 15
<212> TYPE: PRT
<213> ORGANISM: Artificial
<220> FEATURE:

```
<223> OTHER INFORMATION: Ref pep no. 32

<400> SEQUENCE: 56

Leu Glu Leu Lys Gly Ser Glu Thr Thr Phe Met Ser Glu Tyr Ala
1               5                   10                  15

<210> SEQ ID NO 57
<211> LENGTH: 15
<212> TYPE: PRT
<213> ORGANISM: Artificial
<220> FEATURE:
<223> OTHER INFORMATION: Ref pep no. 33

<400> SEQUENCE: 57

Lys Gly Ser Glu Thr Thr Phe Met Ser Glu Tyr Ala Asp Glu Thr
1               5                   10                  15

<210> SEQ ID NO 58
<211> LENGTH: 15
<212> TYPE: PRT
<213> ORGANISM: Artificial
<220> FEATURE:
<223> OTHER INFORMATION: Ref pep no. 34

<400> SEQUENCE: 58

Glu Thr Thr Phe Met Ser Glu Tyr Ala Asp Glu Thr Ala Thr Ile
1               5                   10                  15

<210> SEQ ID NO 59
<211> LENGTH: 15
<212> TYPE: PRT
<213> ORGANISM: Artificial
<220> FEATURE:
<223> OTHER INFORMATION: Ref pep no. 35

<400> SEQUENCE: 59

Phe Met Ser Glu Tyr Ala Asp Glu Thr Ala Thr Ile Val Glu Phe
1               5                   10                  15

<210> SEQ ID NO 60
<211> LENGTH: 15
<212> TYPE: PRT
<213> ORGANISM: Artificial
<220> FEATURE:
<223> OTHER INFORMATION: Ref pep no. 36

<400> SEQUENCE: 60

Glu Tyr Ala Asp Glu Thr Ala Thr Ile Val Glu Phe Leu Asn Arg
1               5                   10                  15

<210> SEQ ID NO 61
<211> LENGTH: 15
<212> TYPE: PRT
<213> ORGANISM: Artificial
<220> FEATURE:
<223> OTHER INFORMATION: Ref pep no. 37

<400> SEQUENCE: 61

Asp Glu Thr Ala Thr Ile Val Glu Phe Leu Asn Arg Trp Ile Thr
1               5                   10                  15

<210> SEQ ID NO 62
<211> LENGTH: 15
<212> TYPE: PRT
<213> ORGANISM: Artificial
<220> FEATURE:
<223> OTHER INFORMATION: Ref pep no. 38
```

<400> SEQUENCE: 62

Ala Thr Ile Val Glu Phe Leu Asn Arg Trp Ile Thr Phe Ser Gln
1               5                   10                  15

<210> SEQ ID NO 63
<211> LENGTH: 15
<212> TYPE: PRT
<213> ORGANISM: Artificial
<220> FEATURE:
<223> OTHER INFORMATION: Ref pep no. 39

<400> SEQUENCE: 63

Val Glu Phe Leu Asn Arg Trp Ile Thr Phe Ser Gln Ser Ile Ile
1               5                   10                  15

<210> SEQ ID NO 64
<211> LENGTH: 15
<212> TYPE: PRT
<213> ORGANISM: Artificial
<220> FEATURE:
<223> OTHER INFORMATION: Ref pep no. 40

<400> SEQUENCE: 64

Leu Asn Arg Trp Ile Thr Phe Ser Gln Ser Ile Ile Ser Thr Leu
1               5                   10                  15

<210> SEQ ID NO 65
<211> LENGTH: 15
<212> TYPE: PRT
<213> ORGANISM: Artificial
<220> FEATURE:
<223> OTHER INFORMATION: Ref pep no. 41

<400> SEQUENCE: 65

Asn Arg Trp Ile Thr Phe Ser Gln Ser Ile Ile Ser Thr Leu Thr
1               5                   10                  15

<210> SEQ ID NO 66
<211> LENGTH: 15
<212> TYPE: PRT
<213> ORGANISM: Artificial
<220> FEATURE:
<223> OTHER INFORMATION: Ref pep no. 42

<400> SEQUENCE: 66

Ile Asn Asn Tyr Lys Asn Pro Lys Leu Thr Arg Met Leu Thr Ala
1               5                   10                  15

<210> SEQ ID NO 67
<211> LENGTH: 15
<212> TYPE: PRT
<213> ORGANISM: Artificial
<220> FEATURE:
<223> OTHER INFORMATION: Ref pep no. 43

<400> SEQUENCE: 67

Tyr Lys Asn Pro Lys Leu Thr Arg Met Leu Thr Ala Lys Phe Tyr
1               5                   10                  15

<210> SEQ ID NO 68
<211> LENGTH: 15
<212> TYPE: PRT
<213> ORGANISM: Artificial
<220> FEATURE:
<223> OTHER INFORMATION: Ref pep no. 47

-continued

```
<400> SEQUENCE: 68

Tyr Lys Asn Pro Lys Leu Thr Arg Met Leu Thr Phe Lys Phe Ala
1               5                   10                  15

<210> SEQ ID NO 69
<211> LENGTH: 15
<212> TYPE: PRT
<213> ORGANISM: Artificial
<220> FEATURE:
<223> OTHER INFORMATION: Ref pep no. 52

<400> SEQUENCE: 69

Tyr Lys Asn Pro Lys Leu Thr Arg Met Leu Thr Ala Lys Phe Ala
1               5                   10                  15

<210> SEQ ID NO 70
<211> LENGTH: 15
<212> TYPE: PRT
<213> ORGANISM: Artificial
<220> FEATURE:
<223> OTHER INFORMATION: Ref pep no. 44

<400> SEQUENCE: 70

Pro Lys Leu Thr Arg Met Leu Thr Ala Lys Phe Tyr Met Pro Lys
1               5                   10                  15

<210> SEQ ID NO 71
<211> LENGTH: 15
<212> TYPE: PRT
<213> ORGANISM: Artificial
<220> FEATURE:
<223> OTHER INFORMATION: Ref pep no. 48

<400> SEQUENCE: 71

Pro Lys Leu Thr Arg Met Leu Thr Phe Lys Phe Ala Met Pro Lys
1               5                   10                  15

<210> SEQ ID NO 72
<211> LENGTH: 15
<212> TYPE: PRT
<213> ORGANISM: Artificial
<220> FEATURE:
<223> OTHER INFORMATION: Ref pep no. 53

<400> SEQUENCE: 72

Pro Lys Leu Thr Arg Met Leu Thr Ala Lys Phe Ala Met Pro Lys
1               5                   10                  15

<210> SEQ ID NO 73
<211> LENGTH: 15
<212> TYPE: PRT
<213> ORGANISM: Artificial
<220> FEATURE:
<223> OTHER INFORMATION: Ref pep no. 45

<400> SEQUENCE: 73

Thr Arg Met Leu Thr Ala Lys Phe Tyr Met Pro Lys Lys Ala Thr
1               5                   10                  15

<210> SEQ ID NO 74
<211> LENGTH: 15
<212> TYPE: PRT
<213> ORGANISM: Artificial
<220> FEATURE:
<223> OTHER INFORMATION: Ref pep no. 49

<400> SEQUENCE: 74
```

Thr Arg Met Leu Thr Phe Lys Phe Ala Met Pro Lys Lys Ala Thr
1               5                   10                  15

<210> SEQ ID NO 75
<211> LENGTH: 15
<212> TYPE: PRT
<213> ORGANISM: Artificial
<220> FEATURE:
<223> OTHER INFORMATION: Ref pep no. 54

<400> SEQUENCE: 75

Thr Arg Met Leu Thr Ala Lys Phe Ala Met Pro Lys Lys Ala Thr
1               5                   10                  15

<210> SEQ ID NO 76
<211> LENGTH: 15
<212> TYPE: PRT
<213> ORGANISM: Artificial
<220> FEATURE:
<223> OTHER INFORMATION: Ref pep no. 46

<400> SEQUENCE: 76

Leu Thr Ala Lys Phe Tyr Met Pro Lys Lys Ala Thr Glu Leu Lys
1               5                   10                  15

<210> SEQ ID NO 77
<211> LENGTH: 15
<212> TYPE: PRT
<213> ORGANISM: Artificial
<220> FEATURE:
<223> OTHER INFORMATION: Ref pep no. 50

<400> SEQUENCE: 77

Leu Thr Phe Lys Phe Ala Met Pro Lys Lys Ala Thr Glu Leu Lys
1               5                   10                  15

<210> SEQ ID NO 78
<211> LENGTH: 15
<212> TYPE: PRT
<213> ORGANISM: Artificial
<220> FEATURE:
<223> OTHER INFORMATION: Ref pep no. 55

<400> SEQUENCE: 78

Leu Thr Ala Lys Phe Ala Met Pro Lys Lys Ala Thr Glu Leu Lys
1               5                   10                  15

<210> SEQ ID NO 79
<211> LENGTH: 15
<212> TYPE: PRT
<213> ORGANISM: Artificial
<220> FEATURE:
<223> OTHER INFORMATION: Ref pep no. 51

<400> SEQUENCE: 79

Lys Phe Ala Met Pro Lys Lys Ala Thr Glu Leu Lys His Leu Gln
1               5                   10                  15

<210> SEQ ID NO 80
<211> LENGTH: 15
<212> TYPE: PRT
<213> ORGANISM: Artificial
<220> FEATURE:
<223> OTHER INFORMATION: Ref pep no. 56

<400> SEQUENCE: 80

```
Ser Leu Glu Glu Glu Leu Lys Pro Leu Glu Glu Val Leu Asn Ala
1               5                   10                  15

<210> SEQ ID NO 81
<211> LENGTH: 15
<212> TYPE: PRT
<213> ORGANISM: Artificial
<220> FEATURE:
<223> OTHER INFORMATION: Ref pep no. 57

<400> SEQUENCE: 81

Glu Glu Leu Lys Pro Leu Glu Glu Val Leu Asn Ala Ala Gln Ser
1               5                   10                  15

<210> SEQ ID NO 82
<211> LENGTH: 15
<212> TYPE: PRT
<213> ORGANISM: Artificial
<220> FEATURE:
<223> OTHER INFORMATION: Ref pep no. 58

<400> SEQUENCE: 82

Lys Pro Leu Glu Glu Val Leu Asn Ala Ala Gln Ser Lys Asn Phe
1               5                   10                  15

<210> SEQ ID NO 83
<211> LENGTH: 15
<212> TYPE: PRT
<213> ORGANISM: Artificial
<220> FEATURE:
<223> OTHER INFORMATION: Ref pep no. 59

<400> SEQUENCE: 83

Glu Glu Val Leu Asn Ala Ala Gln Ser Lys Asn Phe His Leu Arg
1               5                   10                  15

<210> SEQ ID NO 84
<211> LENGTH: 15
<212> TYPE: PRT
<213> ORGANISM: Artificial
<220> FEATURE:
<223> OTHER INFORMATION: Ref pep no. 60

<400> SEQUENCE: 84

Ala Asn Leu Ala Gln Ser Lys Asn Phe His Leu Arg Pro Arg Asp
1               5                   10                  15
```

UNITED STATES PATENT AND TRADEMARK OFFICE
CERTIFICATE OF CORRECTION

| | | |
|---|---|---|
| PATENT NO. | : 10,894,828 B2 | Page 1 of 1 |
| APPLICATION NO. | : 15/324468 | |
| DATED | : January 19, 2021 | |
| INVENTOR(S) | : Onur Boyman, Natalia Arenas-Ramirez and Chao Zou | |

It is certified that error appears in the above-identified patent and that said Letters Patent is hereby corrected as shown below:

In the Claims

In Claim 4, Column 66, Line 61, the word "K96of" should read --K96 of--;

In Claim 14, Column 67, Line 47, the word "SEO ID NO" should read --SEQ ID NO--.

Signed and Sealed this
Twentieth Day of April, 2021

Drew Hirshfeld
*Performing the Functions and Duties of the*
*Under Secretary of Commerce for Intellectual Property and*
*Director of the United States Patent and Trademark Office*